(12) United States Patent
Von Schuckmann

(10) Patent No.: US 8,261,737 B2
(45) Date of Patent: *Sep. 11, 2012

(54) INHALER FOR POWDERY SUBSTANCES

(75) Inventor: Alfred Von Schuckmann, Kevelaer (DE)

(73) Assignee: Alfred von Schuckmann, Kevelaer (DE)

( * ) Notice: Subject to any disclaimer, the term of this patent is extended or adjusted under 35 U.S.C. 154(b) by 999 days.

This patent is subject to a terminal disclaimer.

(21) Appl. No.: 12/224,473

(22) PCT Filed: Mar. 8, 2007

(86) PCT No.: PCT/EP2007/052172
§ 371 (c)(1),
(2), (4) Date: Aug. 27, 2008

(87) PCT Pub. No.: WO2007/104694
PCT Pub. Date: Sep. 20, 2007

(65) Prior Publication Data
US 2009/0050149 A1    Feb. 26, 2009

(30) Foreign Application Priority Data

Mar. 10, 2006 (DE) .......... 10 2006 011 559
Jun. 27, 2006 (DE) .......... 10 2006 029 753

(51) Int. Cl.
*A61M 16/10* (2006.01)
(52) U.S. Cl. .............. 128/203.12; 128/203.15
(58) Field of Classification Search ........... 128/203.12, 128/203.15, 203.19, 203.21, 203.23
See application file for complete search history.

(56) References Cited

U.S. PATENT DOCUMENTS

| 3,598,294 A | 8/1971 | Hedrick et al. |
| 5,113,855 A | 5/1992 | Newhouse |
| 5,239,992 A * | 8/1993 | Bougamont et al. ...... 128/203.15 |
| 5,243,970 A * | 9/1993 | Ambrosio et al. ........ 128/203.15 |
| 5,429,122 A * | 7/1995 | Zanen et al. ............. 128/203.15 |
| 5,524,613 A * | 6/1996 | Haber et al. ............. 128/203.15 |
| 5,617,845 A | 4/1997 | Poss et al. |
| 5,769,073 A * | 6/1998 | Eason et al. ............. 128/203.15 |
| 5,778,873 A | 7/1998 | Braithwaite |
| 5,896,855 A * | 4/1999 | Hobbs et al. ............. 128/203.15 |
| 6,886,560 B1 * | 5/2005 | Seppala ................... 128/203.15 |
| 6,926,003 B2 | 8/2005 | Seppälä |

(Continued)

FOREIGN PATENT DOCUMENTS

CA    2090227    3/1992
(Continued)

OTHER PUBLICATIONS

International Search Report.

*Primary Examiner* — Fenn Mathew
(74) *Attorney, Agent, or Firm* — Collard & Roe, P.C.

(57) ABSTRACT

An inhaler for powdery substances, in particular medical substances, has a substance storage chamber and a dosing chamber, which receives a defined amount of the substance, is formed as a cross-hole of a rod and can be displaced from a filling position into an emptying position, in which emptying position the dosing chamber is located in an air flow channel. The rod has a number of dosing chambers located one after the other on the rod, which preferably move into the emptying position one after the other during a discharge actuation and can be blown out one by one as intermingling small portions (instead of one large one) by positive air pressure in the air flow channel.

19 Claims, 15 Drawing Sheets

U.S. PATENT DOCUMENTS

| | | | |
|---|---|---|---|
| 7,131,441 | B1 | 11/2006 | Keller et al. |
| 7,143,765 | B2 | 12/2006 | Asking et al. |
| 2006/0118106 | A1 | 6/2006 | von Schuckmann |
| 2006/0150971 | A1* | 7/2006 | Lee et al. .................. 128/203.15 |
| 2008/0184999 | A1 | 8/2008 | von Schuckmann |
| 2008/0185000 | A1 | 8/2008 | von Schuckmann |
| 2009/0260626 | A1 | 10/2009 | von Schuckmann |

FOREIGN PATENT DOCUMENTS

| | | |
|---|---|---|
| CA | 2093809 | 2/1993 |
| DE | 40 27 391 | 3/1992 |
| DE | 101 06 788 | 8/2002 |
| DE | 10 2005 033 397 | 1/2007 |
| WO | WO 93/03782 | 8/1993 |
| WO | WO 93/16748 | 9/1993 |
| WO | WO 00/64519 | 11/2000 |
| WO | WO 01/21238 | 3/2001 |
| WO | WO 01/41850 | 6/2001 |
| WO | WO 02/089883 | 11/2002 |
| WO | WO 2004/033009 | 4/2004 |
| WO | WO 2005/016424 | 2/2005 |

* cited by examiner

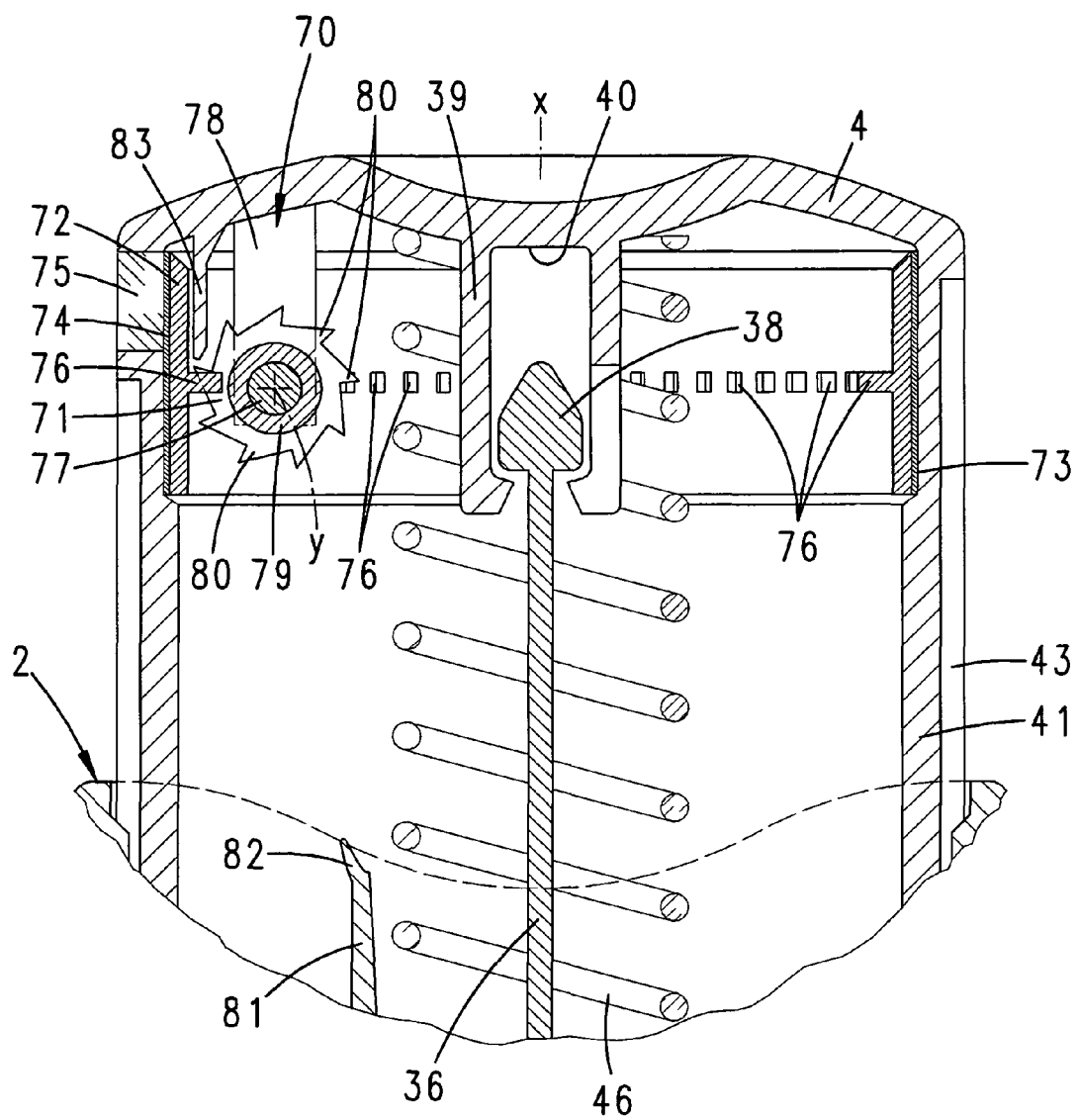

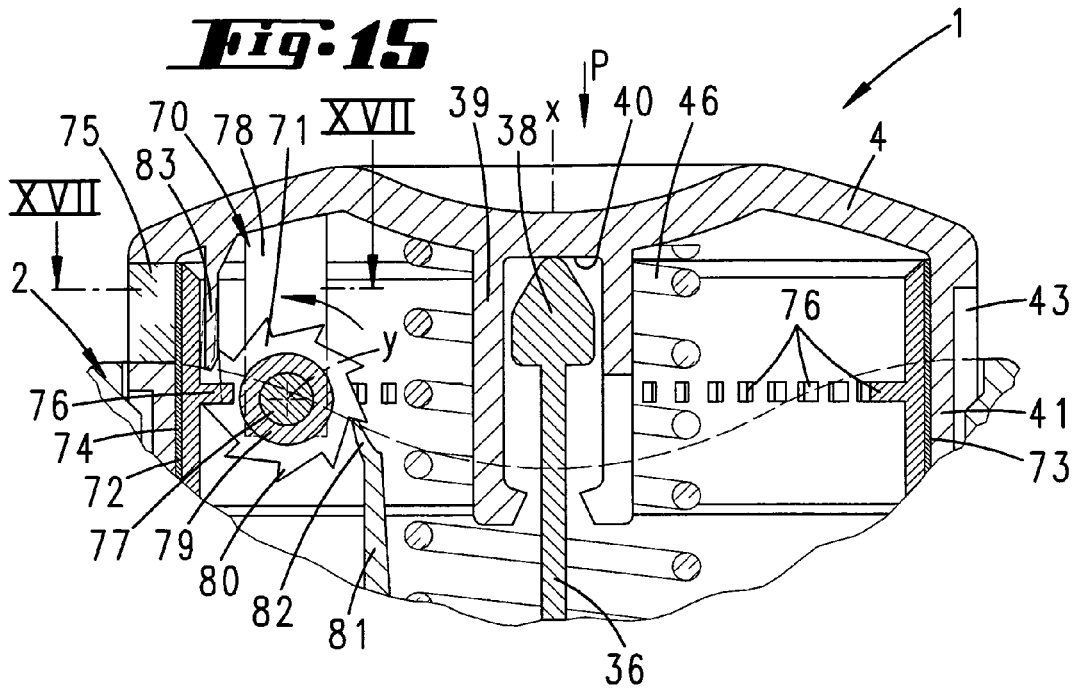
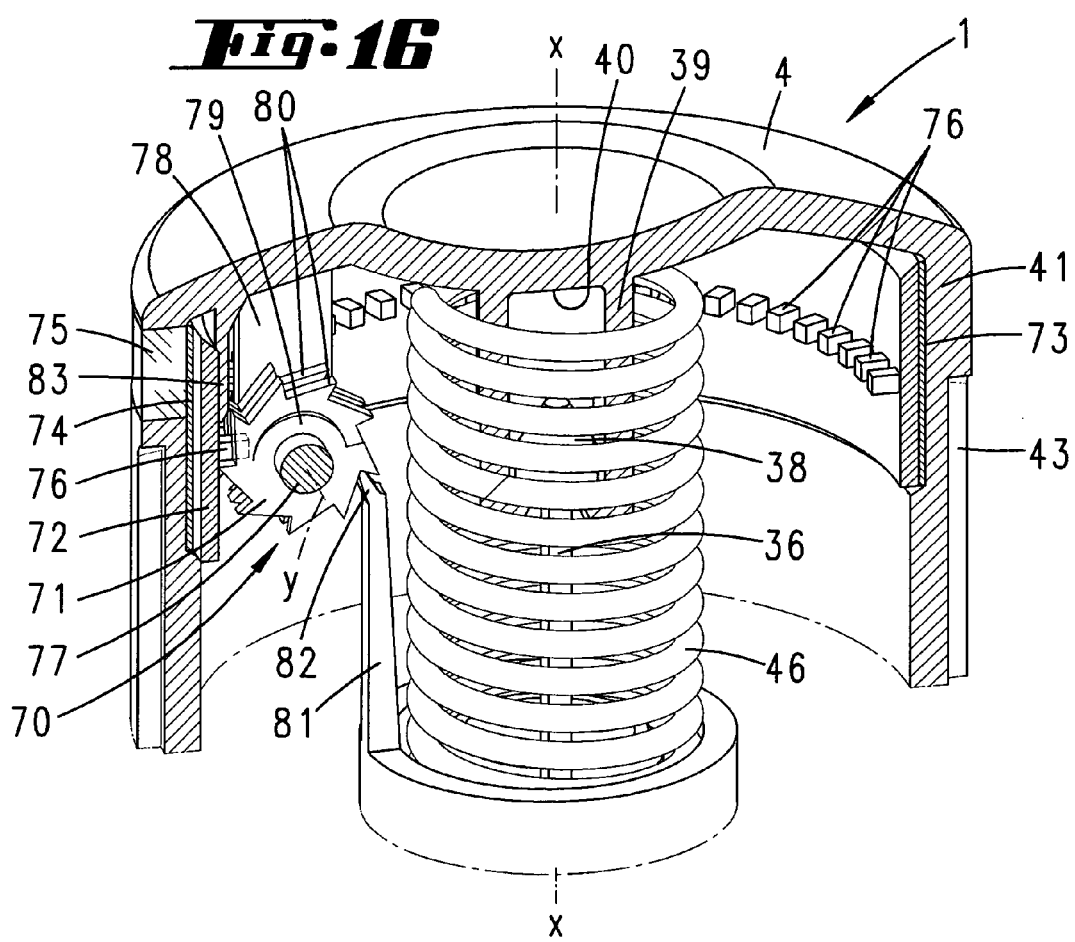

INHALER FOR POWDERY SUBSTANCES

CROSS REFERENCE TO RELATED APPLICATIONS

This application is the National Stage of PCT/EP2007/052172 filed on Mar. 8, 2007, which claims priority under 35 U.S.C. §119 of German Application No. 10 2006 011 559.7 filed on Mar. 10, 2006 and German Application No. 10 2006 029 753.9 filed Jun. 27, 2006. The international application under PCT article 21(2) was not published in English.

The invention relates to an inhaler for powdery substances, in particular medical substances, with a substance storage chamber and a dosing chamber, which receives a defined amount of the substance, is formed as a cross-hole of a rod and can be displaced from a filling position into an emptying position, in which emptying position the dosing chamber is located in an air flow channel.

Inhalers of the type in question are known. Reference is made, for example, to U.S. Pat. No. 5,239,992. This patent specification shows and describes an inhaler that has a rod which comprises a dosing chamber and can be displaced from a filling position into an emptying position. This displacement into the emptying position takes place by a movement attributable to the negative pressure that is produced by the inhalation of the patient through the air flow channel. Dosing chamber displacement and emptying of the dosing chamber are accordingly dependent on suction caused by the patient inhaling deeply.

In view of the known prior art, it is an object of the invention to further improve a generic inhaler in an advantageous way, in particular with regard to the emptying of the dosing chamber in the emptying position.

This object is achieved first and foremost by the subject matter of claim 20, it being provided that the rod has a number of dosing chambers that are located one after the other on the rod, which move into the emptying position one after the other during a discharge actuation and can be blown out one by one by positive air pressure in the air flow channel. This configuration achieves active emptying of each dosing chamber. The dispensing of the substance is similar to that of inhalers provided with aerosol cartridges. The positive air pressure has the effect that the apportioned substance is actively expelled from the dosing chamber, the arrangement of a number of dosing chambers that lie in a row and pass the emptying position one after the other in the longitudinal extent of the rod comprising the dosing chambers in the course of its displacement having the effect that the substance is blown out by the air rather like the action of a machine gun. On account of the active blowing out of the dosing chamber or dosing chambers, inhalation of the substance can be reliably carried out even if, for example, the patient is incapable of producing a sufficient suction air stream for the displacement and emptying of a dosing chamber that is usually relatively large, as known from the prior art. In addition, the blowing out of the dosing chambers under air pressure achieves extremely fine distribution of the substance delivered, which in turn makes it possible to use micronized powder substances, which are designed for direct access to the lungs. This also makes it possible for the size of the dosing chambers to be chosen such that each chamber can receive approximately 0.03 to 0.2 mg of substance.

In a preferred development, it is provided that the suction air stream necessary for inhaling the substance to be discharged does not flow directly around or through the emptying region of the air flow channel, that is to say the region through which the rod passes and which is provided with the dosing chambers. Rather, when inhaling takes place, the suction air stream under negative pressure is only applied in the region of a mixing portion to be associated with the mouth or the nose, into which mixing portion the divided-up substance is actively propelled by means of the positive air pressure.

The subject matters of the further claims are explained below with reference to the subject matter of claim 1, but may also be of importance in their independent formulation.

For instance, it is provided in a development of the subject matter that the rod is formed as a flat rod, with a length measured in cross-section that corresponds to a multiple of, for example ten to twenty times, the width measured transversely thereto. For instance, a rod with a thickness of approximately 0.3 to 0.7 mm, preferably 0.5 mm or 0.3 mm, is preferably provided. The flat rod may consist of a plastics material, in particular of a rigid plastics material. A solution in which the flat rod is produced from a metallic material is preferred. The dosing chambers lying one after the other in the longitudinal extent of the flat rod are provided in the simplest way as holes in the form of circular disks in plan view, each with a center axis aligned perpendicularly to the flat sides of the flat rod.

The rod passes through the substance storage chamber, in particular with the portion of the rod comprising the dosing chambers, which are thereby immersed in the powdery substance that is kept in the storage chamber. The storage chamber wall here preferably consists of an elastic material, such as for example a rubber-like material, further for example of a thermoplastic elastomer. When the inhaler is actuated, this elastically-adapted storage chamber wall is made to curve in the direction of the rod and consequently in the direction of the dosing chambers. This initially takes place by the storage chamber wall being subjected to a positive pressure acting on it radially from the outside, which positive pressure also serves for emptying the dosing chambers in the emptying position. This positive pressure is built up in the course of inhaler actuation, preferably in the form of a positive air pressure. In this respect, it is further provided that the storage chamber wall is made to curve, at least in the region of the dosing holes, until it abuts against the rod and so has the effect of pressing the substance that is kept in the storage chamber into the dosing chambers. In the curved-in state, portions of the storage chamber wall abut each flat side of the rod, facing the respective opening cross-sections of the dosing chambers. In this abutting position, the portions of the storage chamber wall act with a wiping effect in the course of a displacement of the rod into the emptying position. Such wiping for exact apportioning of the substance to be discharged takes place more preferably even before the emptying position is reached.

In a preferred configuration of the subject matter of the invention, in addition to being subjected to positive pressure in the way described, the storage chamber wall is actively made to curve in the direction of the rod. Provided for this purpose are thrust pieces, which act on the storage chamber wall from the outside, for the preferred abutment of portions of the wall on the flat sides of the rod. Actively subjecting the chamber wall to the effect of the thrust pieces in this way further assists the filling of the dosing chambers formed in the centrally held rod.

The displacement of the rod comprising the dosing chamber into the emptying position and the application of pressure to the storage chamber wall for filling the dosing chambers take place each time the inhaler is actuated. In this respect, an inactive displacement is provided between the inhaler actuating button and the rod, with the effect that the inward curving of the storage chamber wall by means of the outer thrust pieces, and optionally the application of air pressure, takes place before the rod is taken along. Accordingly, the dosing chambers are filled by means of the thrust pieces, with the storage chamber wall in between, preferably while the rod is still in the rest position. Only after this filling and the associated completion of the inactive displacement is the rod carried along by further displacement of the actuating button, to bring the dosing chambers into the emptying position.

The thrust pieces are preferably provided with jaws, which have abutting faces which lie parallel to the wide-side wall surface of the rod in the fully pivoted-in or pressed-on position of the thrust pieces, one result of which is that the dosing chambers are correctly filled. Another result of this is that a wiping position is achieved. The abutting faces on the jaws are correspondingly of a flat planar form.

The actuating button of the inhaler is formed such that it protrudes at the head of the inhaler housing above the latter and can be displaced against a return spring. This allows the inhaler as a whole to be preferably held between the thumb and, for example, the middle finger, the middle finger resting on the actuating button and the thumb being supported on the surface of the housing that is opposite from the actuating button. The inhaler is actuated by pressing the actuating button, the thrust pieces being pivoted in the direction of the rod by means of run-on slopes of the actuating button. After a short inactive displacement, the actuating button pushes the rod before it while displacing the dosing chambers from the filling position in the storage chamber into the emptying position. With the thrust pieces disposed in a pivotable arrangement, the run-on slopes of the actuating button correspondingly act on the latter in a pivoting manner. As an alternative to this, the thrust pieces may also be disposed such that they can be displaced strictly linearly in a radial direction, this radial displacement toward the rod being achieved by means of a wedge-like action. In particular in the case of a pivoting configuration of the thrust pieces, they are formed in a self-returning manner, for instance in particular by appropriate spring characteristics of the arms carrying the thrust pieces. The thrust pieces correspondingly move back into their original position again after the load acting via the run-on slopes is no longer exerted, thereby releasing the storage chamber wall, which returns again into the original position on account of the elastic properties.

With active displacement of the actuating button in the inhaler housing, a positive air pressure is built up, which proceeds to blow out the substance by displacement of the rod into the air flow channel, specifically the part of the flow channel adjoining the rod in the direction of flow.

Accordingly, the positive pressure is only reduced, at least partly, by a displacement of the dosing chamber into the air flow channel, with the substance being blown out. Further corresponding to the way in which a number of dosing chambers are disposed one after the other in the rod and the respective dosing chamber is accordingly connected to the air flow channel in a successive manner, the partial reduction of the positive air pressure, with the substance being fired out from the respective dosing chamber, takes place in a staccato manner, which brings about optimum blowing-out of the substance and cloud-like discharge to the surroundings and to the air stream produced by inhaling.

The positive air pressure to be built up for blowing out is achieved by a piston/housing arrangement. This is achieved by an elastic piston ring at the inward end region of the cup-shaped wall of the actuating button, which interacts with an inner wall of the outer inhaler housing, which outer housing correspondingly forms a compressed-air cylinder for the piston ring. The actuating button itself forms the piston area on the inner wall. In a preferred arrangement, the thrust pieces and the storage chamber are disposed in the region of the compressed-air cylinder created in this way, which assists the way in which the storage chamber is acted upon from the outside and the thrust pieces are displaced into the dosing-chamber filling position.

The linearly displaceable rod comprising the dosing chambers has the character of a valve. The cross-section of the rod closes the air outlet in the region of the air flow channel, as a result of which the positive air pressure can build up in the course of the downward displacement of the actuating button, facing away from the discharge side of the air flow channel. Only when a dosing chamber of the rod is moved into the air flow channel is the action of valve-like opening, and corresponding blowing-out under compressed air, brought about. If the dosing chambers are appropriately spaced apart from one another in the direction of movement of the rod, brief closing of the flow path by the solid material of the rod between two dosing chambers always takes place between the valve-opening-like blowing-out phases of the dosing chambers.

Disposed between the air-outlet closing point, which is formed by the interacting region of the air flow channel and the rod passing transversely through it, and the housing space accommodating the storage chamber, or compressed-air cylinder, is an air inlet valve, which, in the course of a spring-assisted return displacement of the actuating button and corresponding enlargement of the cylinder space created, allows replenishing air to flow in, but in the course of active actuation for discharge of an inhalation substance is closed.

A development of the subject matter of the invention that proves to be particularly advantageous is one in which a setting device is provided for determining the number of dosing chambers that can be brought into the emptying position. For instance, in particular in the case of such a configuration, a number of dosing chambers, for example three to ten or more, are provided in the rod such that they are located one after the other, evenly spaced apart in relation to one another, as seen in the direction of displacement. Metering can be chosen as needs be, thus limiting the displacement of the rod in the longitudinal extent. Depending on the metering-dose needed, only a few dosing chambers or more dosing chambers are accordingly brought into the emptying position, that is to say into the region where they are subjected to the blowing-out effect of the compressed air. On account of the small quantities of substance per dosing chamber, very accurate, variable dosing can be achieved. For example, an accessible setting ring that is provided with a number of steps is provided for stopping the displacing movement of the actuating button. In a way corresponding to the stop-limited displacement path of the button, a specific number of dosing chambers pass through the emptying position. For interacting with the steps on the setting side, the actuating button is provided with counter-means, for instance preferably with a stop lug.

By reducing the cross-section of the air flow channel, in particular of the end portion facing the blowing-out end, a nozzle-like configuration can be achieved. For instance, such a reduced cross-section of an air flow channel end portion corresponds approximately to 0.5 to 0.9 of the original cross-section. In a development of the subject matter of the invention, it is provided that the air flow channel directed straight across continues into an obliquely upwardly directed end channel portion of smaller cross-section, which is set back within a nose tube and ends at the free end of the latter. As a result of this configuration, the proposed inhaler can also be used for nasal application. As a result of the active emptying of the dosing chambers, the medicament to be inhaled is blown out specifically into the nasal cavity. Simultaneous inhalation through the nose advantageously assists the further distribution of the medicament. The obliquely upwardly directed alignment of the end channel portion, and consequently also of the nose tube accommodating this end channel portion, has the effect that the inhaler can be comfortably used, for instance also optionally with virtually vertical alignment of the inhaler axis during the inhalation process.

To provide the user with a means by which it is possible to check the filling level or the amount dispensed, an indexing mechanism actuated when the blowing-out air pressure is reached is provided in a development of the subject matter of the invention. Such an indexing mechanism counts each individual actuation of the inhaler in which a discharge of medicament takes place. For instance, such an indexing mechanism has a scale, for example a scale ring, on which either the inhalation events that have already been carried out are indicated or alternatively, counting down from a maximum number of inhalations, indicating the inhalation shots still available. The indexing mechanism is actuated in dependence on reaching the blowing-out air pressure, which blowing-out air pressure is built up directly before the filled dosing chamber reaches the transfer region with respect to the air flow channel. Accordingly, the indexing mechanism is switched directly before transfer of the medicament into the air flow channel, and accordingly directly before active blowing-out of the medicament. If, on the other hand, the trigger is only actuated to the extent that firing-out of the medicament does not occur, that is to say optionally only for filling the dosing chambers followed by return displacement of the trigger, no switching of the indexing mechanism takes place. In a configuration given by way of example, this is initiated by a counting finger acting on the indexing mechanism, the tip of which finger reaches the indexing wheel of the indexing mechanism approximately at the beginning of the displacement of the rod with the filled dosing chambers into the region of the air flow channel. The counting finger is correspondingly positioned at a distance from the indexing wheel, which distance is overcome by actuation of the trigger with accompanying displacement of the rod comprising the dosing chambers and simultaneous building-up of the blowing-out air pressure.

In a preferred configuration, the indicator of the indexing mechanism is a scale ring which is aligned concentrically in relation to the inhaler axis and is formed on the inside in the manner of a toothed ring for step-by-step displacement in the circumferential direction of rotation, for interaction with the indexing wheel. In a preferred configuration, the latter is formed in such a way that it turns the scale ring of the indexing mechanism in the manner of a worm wheel. Accordingly, no further intermediate transmissions are needed for transforming the actuation of the indexing wheel by the finger of the indexing mechanism, based on a linear movement, into a circular movement directed transversely in relation to the axis. Depending on the configuration, in particular of the indexing mechanism, the transmission to the scale ring may be stepped down or stepped up.

The invention is explained in more detail below on the basis of the accompanying drawing, which merely represents a number of exemplary embodiments and in which:

FIG. 14 shows the region XIV in FIG. 13 in an enlarged representation;

FIG. 15 shows a representation substantially corresponding to FIG. 14, but in an actuating position of the inhaler in which the indexing mechanism is actuated by a counting finger;

FIG. 16 shows a perspective partial sectional representation according to FIG. 15;

Figure 1:
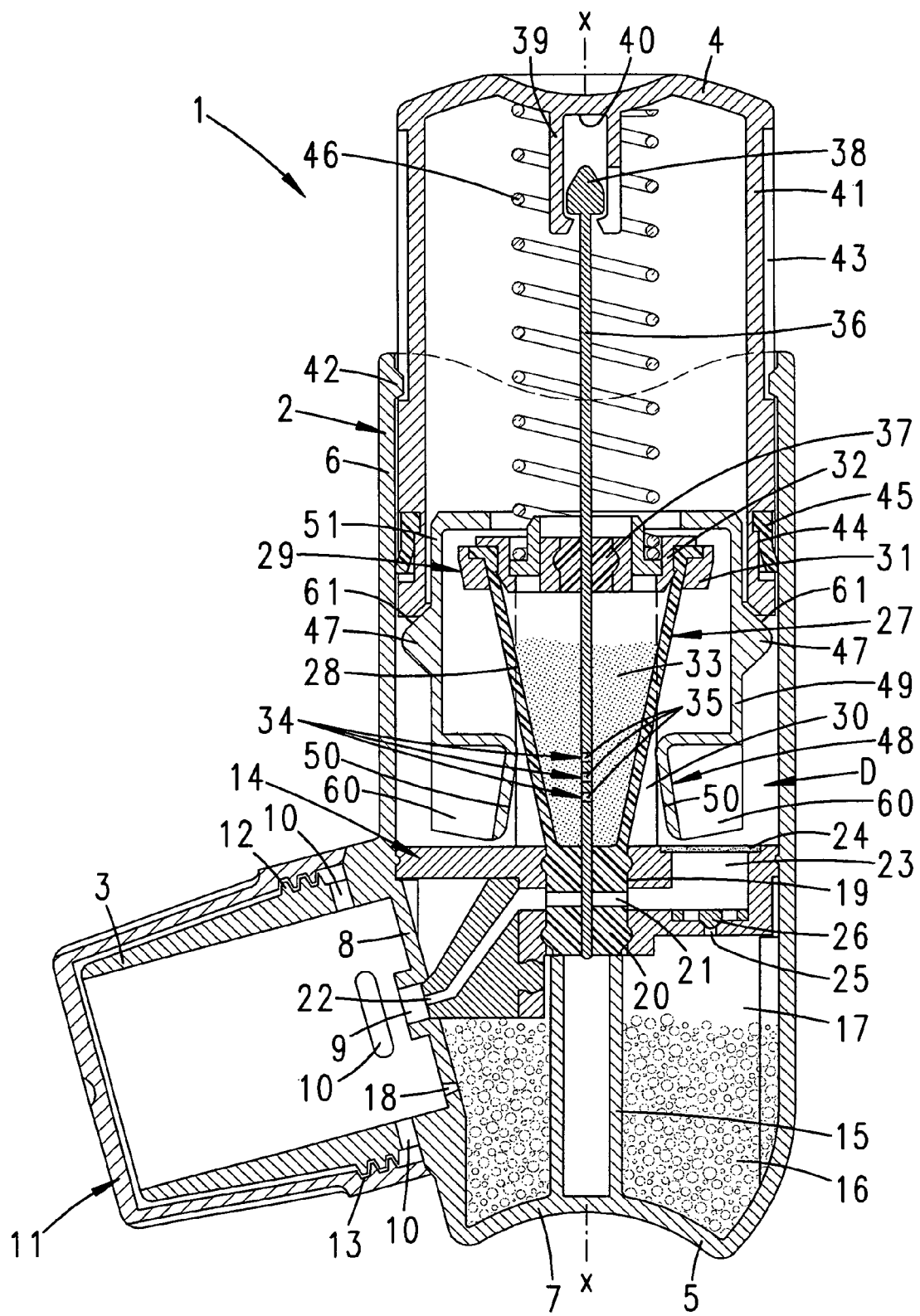
FIG. 1 shows a vertical section through an inhaler for powdery substances in a first embodiment, for the unloaded initial position.

Shown and described is an inhaler 1, which is realized as a conveniently portable pocket device, with a cylindrical housing 2, from which an approximately radially protruding mouthpiece 3 extends. The general form of the inhaler 1 corresponds substantially to that of the inhalers provided with aerosol cartridges. The way in which the inhaler 1 is handled has also been correspondingly adopted and is immediately evident to the user.

The inhaler 1 therefore has an actuating button 4, which accommodates the general housing axis x, is aligned transversely in relation to this axis x, protrudes above the housing 2 and is opposed by a counter-face 5 at the foot of the housing. A discharge of substance is achieved by displacement of the actuating button 4 along the axis x in the direction of the counter-face 5 on the underside.

The housing 2 is formed as a hollow-cylindrical body, with a circular shape in plan view in the exemplary embodiment that is represented. Other forms deviating from this circular form in plan view are also conceivable, for example also elliptical or polygonal forms.

The circular-cylindrical outer inhaler housing 6 is closed at the foot by an inhaler bottom 7, which forms the counter-face 5 for the actuation of the inhaler 1. Toward the side opposite from this bottom 7, the housing 2 is of an open form.

In the foot region of the housing 2, the mouthpiece 3 extends from the latter in approximately radial direction, for instance more specifically in the exemplary embodiment represented with the inclusion of an acute angle of approximately 75 to 80° in relation to the inhaler axis x, which mouthpiece is substantially formed as a hollow cylindrical body, with an opening facing axially outward with respect to the alignment of the mouthpiece 3. A mouthpiece bottom 8 disposed in the transitional region from the housing 2 into the mouthpiece 3 has a central opening 9.

At an axial spacing from this central bottom opening 9, air-inflow openings 10 are formed in the mouthpiece wall along a circumferential line, disposed in an evenly distributed manner, for the air-flow connection of the interior space of the mouthpiece associated with the bottom opening 9 to the surroundings.

When the inhaler 1 is not in use, the mouthpiece 3 is covered over by a screw cap 11. For this purpose, the mouthpiece 3 is provided on the outer lateral wall with an external thread 12, which interacts with an internal thread 13 of the cap 11. The lateral portion of the screw cap 11 comprising the internal thread 13 engages over the air-inflow openings 10 of the mouthpiece 3 in the closure position, the annular end face of this lateral portion of the screw cap 11 also coming up against a housing portion in a stop-limited manner.

The housing 2 is subdivided transversely in relation to the housing axis x by a carrier 14 secured to the inner wall of the housing at the level of the transition from the housing to the mouthpiece 3. An upper housing portion with respect to the carrier 14 and a lower portion, associated with the counter-face 5, are accordingly obtained, said lower portion being passed through centrally by a supporting tube 15, which extends in the axial direction and on which the carrier 14 is seated. A moisture-absorbing material 16 is accommodated in the annular space thereby created in the lower housing portion. Furthermore, this annular space 17 is in communication with the cylindrical interior space of the mouthpiece 3 via a replenishing flow opening 18, which is formed in the region of the mouthpiece bottom 8, and with the surroundings via the air-inflow openings 10.

The disk-shaped, solid carrier 14 has a central receptacle 19, in which a sealing element 20 consisting of a thermoplastic material is fitted. This sealing element 20 sits in the receptacle 19 in the manner of a plug, the carrier 14 also being supported by means of this sealing element 20 on the tube 15.

The sealing element 20 is provided with an air flow channel 21, which is aligned substantially straight across in relation to the axis x and is continued on both sides, respectively passing through the carrier 14. The air flow channel 21 therefore extends on one side of the sealing element 20 such that it passes through the carrier 14 as far as the central opening 9 of the mouthpiece bottom 8, to form an air outlet 22. In the opposite direction with respect to the sealing element 20, the air flow channel 21 continues, with its cross-section widening, as far as the upper portion of the housing that is cut off by the carrier 14. The corresponding channel opening 23 is formed on the wide face of the carrier 14 facing the upper housing portion, this channel opening 23 also being covered by a filter element 24.

The air flow channel 21 is consequently subdivided into a channel portion on the mouthpiece side and a portion on the housing side. In the latter, the filter-covered channel opening 23 is formed. Also disposed in this portion is a replenishing flow opening 25, which lies opposite the channel opening 23 and forms a link between the portion of the air flow channel 21 on the housing side and the annular space 17 formed on the underside of the carrier 14. This replenishing flow opening 25 is covered over by an air inlet valve 26, which is set up in such a way that the replenishing flow opening 25 is only opened when there is an air flow from the annular space 17 through the air flow channel 21 in the direction of the upper housing portion. In the opposite direction of air flow, the valve 26 closes this replenishing flow opening 25.

The air flow channel 21 is made much smaller than the free cross-section of the mouthpiece 3, in particular in the region of the sealing element 20 and of the portion facing the mouthpiece 3. For instance, the free diameter of the interior space of the mouthpiece 3 corresponds approximately to ten to thirty times the diameter of the air flow channel 21, which latter is formed in a tapering manner, in particular from the sealing element 20 in the direction of the opening 9 on the mouthpiece side, in the region of an obliquely downwardly extending portion, to form a nozzle-like channel.

The sealing element 20 merges in one piece, of the same material, into a funnel-shaped storage chamber 27 that is facing the upper housing portion and has a cross-section widening upward, that is to say in the direction of the housing opening at the end face. The storage chamber wall 28 correspondingly also consists of a thermoplastic elastomer or some other rubber-like material.

The free end of the storage chamber 27 of a widened diameter is held by a holder 29, which is aligned transversely in relation to the inhaler axis x and is secured to the carrier 14 enclosing the lower end of the storage chamber 27 by means of supports 30, the supports extending to the sides of the storage chamber 27 and being disposed opposite one another. The axial distance between the ends of the storage chamber is accordingly fixed.

The upper free end of the storage chamber 27 is held in the holder 29 in a sealing manner, for instance in the exemplary embodiment represented is clamped in between a radially outer holding ring 31 and a radially inner, plug-like holding portion 32.

Kept in the storage chamber 27 is a micronized powdery substance 33, which is intended to be inhaled in an apportioned discharge by means of the proposed device.

For the apportioned discharge of the substance 33, dosing chambers 34 are provided, for instance three in the first embodiment that is represented. The size of each dosing chamber 34 defines the amount of substance respectively to be delivered.

The dosing chambers 34 are formed as cross-holes 35 of a rod 36, which is formed as a flat rod and extends centrally along the axis x. Here, the cross-holes 35 pass through the wide-side wall surfaces of the flat rod 36, the latter also having in cross-section a width/length ratio of 1:5 to 1:20. In the exemplary embodiment represented, a flat rod thickness of approximately 0.5 mm is chosen, with a length measured transversely thereto of approximately 3 to 3.5 mm. The cross-holes 35 are chosen in their diameter such that a dosing chamber 34 respectively formed thereby receives an amount of substance of from 0.05 mg to 0.1 mg.

The rod 36 with the dosing chambers 34 passes through the storage chamber 27 centrally in the direction of extent of the axis x. At the foot of the storage chamber 27, the rod 36 also passes through the sealing element 20 while crossing the air flow channel 21 formed in the latter; as a result of this configuration, closure of the air flow channel 21 is initially achieved by means of the rod 36.

In the opposite direction from this, the rod 36 extends beyond the storage chamber 27, while passing through the holder 29 defining the storage chamber 27. Disposed in the region where it passes through the holder 29 is a further sealing element 37, which like the sealing element 20 in the foot region of the storage chamber 27 acts on the surfaces of the rod 36 in a wiping manner, while at the same time sealing the zones that are passed through.

In an initial position of the inhaler 1 according to the representation in FIG. 1, the dosing chambers 34 disposed one after the other and uniformly spaced apart in relation to one another in the longitudinal extent of the rod 36 are positioned in the lower third of the storage chamber 27, surrounded by the stored substance 33.

The spacing of the dosing chambers 34 from one another substantially corresponds approximately to the diameter of a cross-hole 35 forming a dosing chamber 34.

The free end of the rod 36, protruding upward above the storage chamber 27, is provided with a driver 38 similar to the head of a mushroom. This is held by drag arms 39, which are formed onto the underside of the actuating button 4 and have a length that corresponds approximately to twice the length of the driver 38 in the direction of extent of the axis x. In this way, an inactive displacement is created between the tip of the driver 38 that is facing the actuating button 4 and the driving face 40 that corresponds to the tip and is on the underside of the actuating button 4.

The actuating button 4, extending substantially transversely in relation to the inhaler axis x, merges into a cylindrical portion that is formed concentrically in relation to the axis x and has a cup-shaped wall 41, which enters the housing 2 with its opening facing down. The outside diameter of the wall 41 is correspondingly adapted to the inside diameter of the cylindrical portion 6 of the housing. The actuating button 4 can be pushed into the housing 2 with its wall 41 being guided by the cylindrical portion 6, this taking place with stop limitation in the respective end positions.

To realize this stop limitation, the cylindrical portion 6 of the housing has in the region of its free peripheral portion two diametrically opposed, radially inward-facing guide lugs 42, which engage in axially parallel grooves 43 in the region of the outer lateral surface of the wall 41. This also achieves the effect of preventing the housing 2 from twisting with respect to the actuating button 4.

In the region of the free end of the wall 41 of the actuating button protruding into the housing 2, an annular groove 44 is provided on the outer lateral wall, for accommodating a piston ring 45 consisting of an elastomer material, which comes up against the inner wall of the cylindrical portion 6 of the housing for sealing purposes.

Helping to maintain the initial position of the actuating button according to the representation in FIG. 1 is a helical return spring 46, which acts on the underside of the actuating button 4 and, while surrounding the rod 36 and the drag arms 39 of the actuating button 4, is supported at the other end on the holder 29 forming the termination at the head of the storage chamber 27. This initial position is defined by the guide lugs 42 coming up against the lower end of the grooves 43 on the actuating button, the driver 38 on the rod also assuming its maximum distance from the driving face 40 of the actuating button 4 in this initial position.

Extending into the displacement path of the wall 41 of the actuating button are wedge-shaped disengaging projections 47 with upwardly facing run-on slopes 61 of two diametrically opposed arms 49, which in the free end region at the foot carry radially inwardly protruding thrust pieces 48. These arms 49, provided with the thrust pieces 48, are positioned in relation to the supports 30 carrying the holder 29 such that they are offset by 90° in plan view; they are also secured to the supports by means of a carrier on the holder 29 that is in the form of a circular ring in plan view. The arms 49 and the thrust pieces 48 forming radially inwardly facing abutting faces 50 of the jaws 60 extend in a plan view, or in a cross-section through the inhaler 1, parallel to and at a distance from a wide-side face of the rod 36. Accordingly, the abutting faces 50 are positioned such that they are facing the wide-side faces of the rod 36, the abutting faces 50 also being respectively formed in a planar manner.

Particularly the arms 49, also particularly the articulating regions 51 on the carrier in the form of a circular ring, are chosen with respect to material selection and/or with respect to material thickness so as to allow radially inward pivoting in the direction of the axis x about the articulating regions 51. The resilient properties of the plastics material chosen are used for the automatic return of the arms 49 into the original position.

The length of the arms 49, measured in the axial direction, is chosen such that the thrust pieces 48 provided at the ends extend approximately at the level of the lower third of the storage chamber 27.

The inhaler 1 functions as follows:

By applying pressure (represented by the arrow P) to the actuating button 4, the latter is lowered into the housing 2 along the axis x in a slidingly displaced manner. The housing 2 and, as a result of the sealing by means of the piston ring 45, the cup-like actuating button 4 form a compressed-air cylinder D, in which a positive air pressure is built up as the actuating button 4 is lowered. Here, the underside of the actuating button 4, lying on the inside, forms the piston area.

Figure 2:
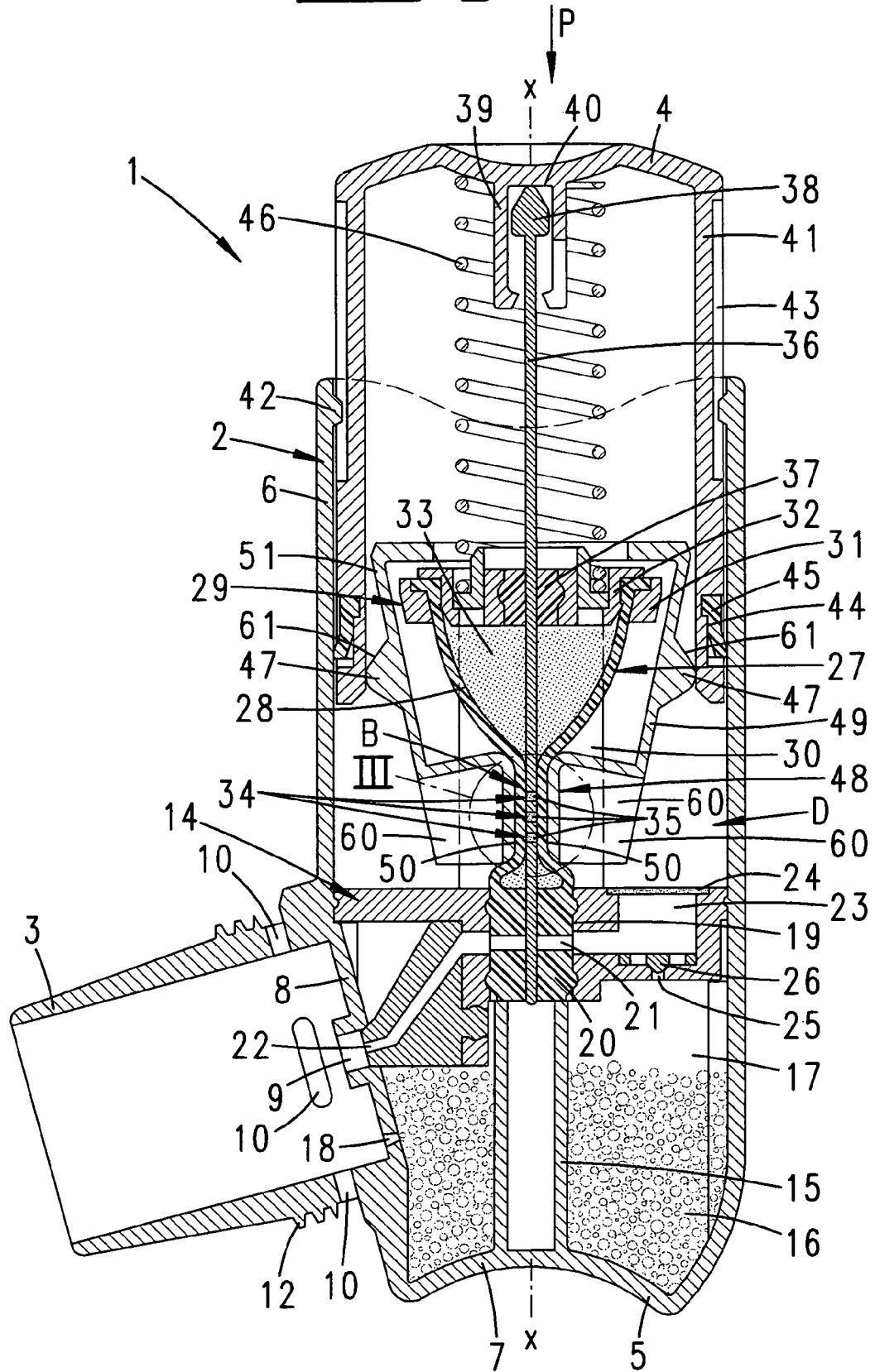
FIG. 2 shows a sectional representation corresponding to FIG. 1, but after removal of a protective mouthpiece cap, for a first intermediate position in the course of actuation of the inhaler, in which dosing chambers are filled with the substance.
Figure 3:
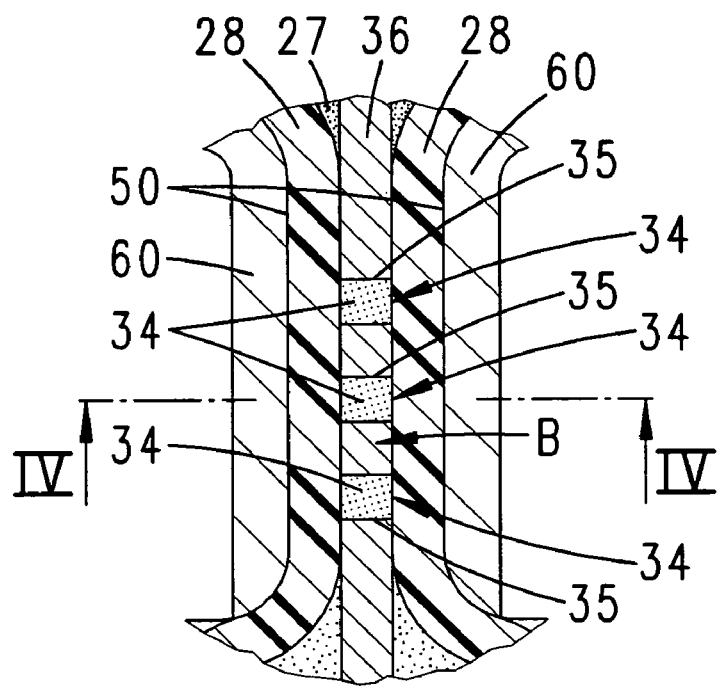
FIG. 3 shows the enlargement of the region III taken from FIG. 2.
Figure 4:
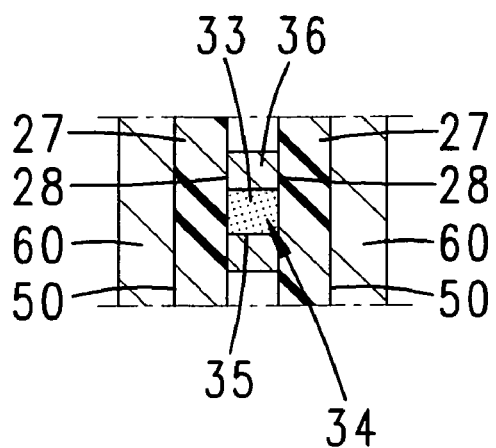
FIG. 4 shows the section along the line IV-IV in FIG. 3.

Moreover, in the course of the downward movement of the actuating button 4, the disengaging projections 47 are acted upon by means of the edge at the end face of the wall 41 that is provided with a corresponding bevel, which leads to an inward pivoting of the arms 49 about the articulating regions 51 as the button 4 is lowered further. As a result of this, the thrust pieces 48 pivot radially inward about a radius in relation to the articulating regions 51, with the storage chamber wall 28 being made to curve inward into the filling position B according to the representation in FIG. 2, in which the abutting faces 50 come into parallel alignment with one another and with the wide-side faces of the rod 36, in which position, with the respective portions of the storage chamber wall inbetween, portions of substance are pressed into the dosing chambers 34. The substance that is present on both sides of the dosing chamber openings in the initial position of the inhaler 1 is forced into the cross-holes 35 by means of the storage chamber wall 28 and the thrust pieces 48 acting on the latter, after which the substance is held of its own accord in the dosing chambers 34, in particular in the case of a micronized powder substance.

The inward curving of the storage chamber wall 28 for pressing the substance into the dosing chambers 34 is assisted by the positive air pressure in the compressed-air cylinder D that builds up in the course of this process.

Until the dosing chambers 34 are filled completely, the rod 36 remains in its initial position, this being attributable to the inactive displacement provided in the region of the drag arms 39. Only after this filling of the dosing chambers does the driving face 40 that is formed on the underside of the button come up against the driver 38 on the end of the rod, to drag the rod 36 along in the further downward displacement of the actuating button 4.

In the course of this downward rod displacement after filling of the dosing chambers, the filled dosing chambers 34 successively come into line with the air flow channel 21, which until then is closed in a slide-like manner by the closed, solid end portion of the rod 36, which makes it possible for the pressure to build up. When a dosing chamber 34 reaches the air flow channel 21 (emptying position E), the valve created in this way is briefly opened. The cross-hole 35 forming the dosing chamber 34 becomes part of the air flow channel 21. The built-up positive air pressure causes the apportioned substance to be abruptly blown out from the dosing chamber to inject this portion via the air outlet 22 into the mouthpiece 3, which latter is enclosed by lips during actuation of the inhaler 1 in such a way that the air-inflow openings 10 are not covered. By inhaling, ambient air is sucked in via these air-inflow openings 10, the ambient air being supplemented with the injected cloud of apportioned substance.

In a way corresponding to the arrangement represented in the exemplary embodiment of three dosing chambers 34 provided one after the other, very rapid expulsion of the substance portions takes place, respectively boosted for a short time by compressed air, in dependence on the speed of the downward displacement of the actuating button 4.

In the course of the downward displacement, the free end of the rod 36 extending down in the axial direction enters the interior space of the supporting tube 15.

The end position of the actuating button 4, as viewed in the direction of downward displacement, is likewise stop-limited. This is effected by the guide lugs 42 coming up against the upper peripheral region of the grooves 43 interacting with them and/or by the free annular end face of the wall 41 of the actuating button coming up against the surface of the carrier 14.

By no longer applying pressure to the actuating button 4, the latter automatically returns into the initial position together with the dragged-along rod 36, as a result of the spring force that has built up. This is accompanied by release of the arms 49 comprising the thrust pieces 48, which on account of the spring characteristics of the material chosen also accordingly pivot back into their original position.

In the course of the return displacement of the actuating button 4 and the accompanying enlargement of the volume of the compressed-air cylinder D, replenishing air is sucked in. This takes place via the replenishing flow openings 18 and 25, with the moisture-absorbing material 16 being flowed through, when the air inlet valve 26 is correspondingly opened.

As a result of the funnel-shaped configuration of the storage chamber 7, the substance is automatically replenished by material slipping down when the external load acting on the storage chamber wall 28 by means of the thrust pieces 48 is no longer exerted, such replenishment of the substance also being assisted by flexing caused by influencing of the storage chamber wall 28 by inward curving.

With the exception of the elements having sealing properties and the storage chamber 27, optionally also with the exception of the component with arms 49 and thrust pieces 48 having spring characteristics, the inhaler 1, in particular the housing and the actuating button 4 with the wall 41 as well as the holder 29 with the carrier 14, is produced from a plastics material, more particularly produced from a rigid plastics material. The rod 36 may also consist of such a rigid plastics material. In this respect, however, a rod 36 of a metal material is preferred.

Figure 12:
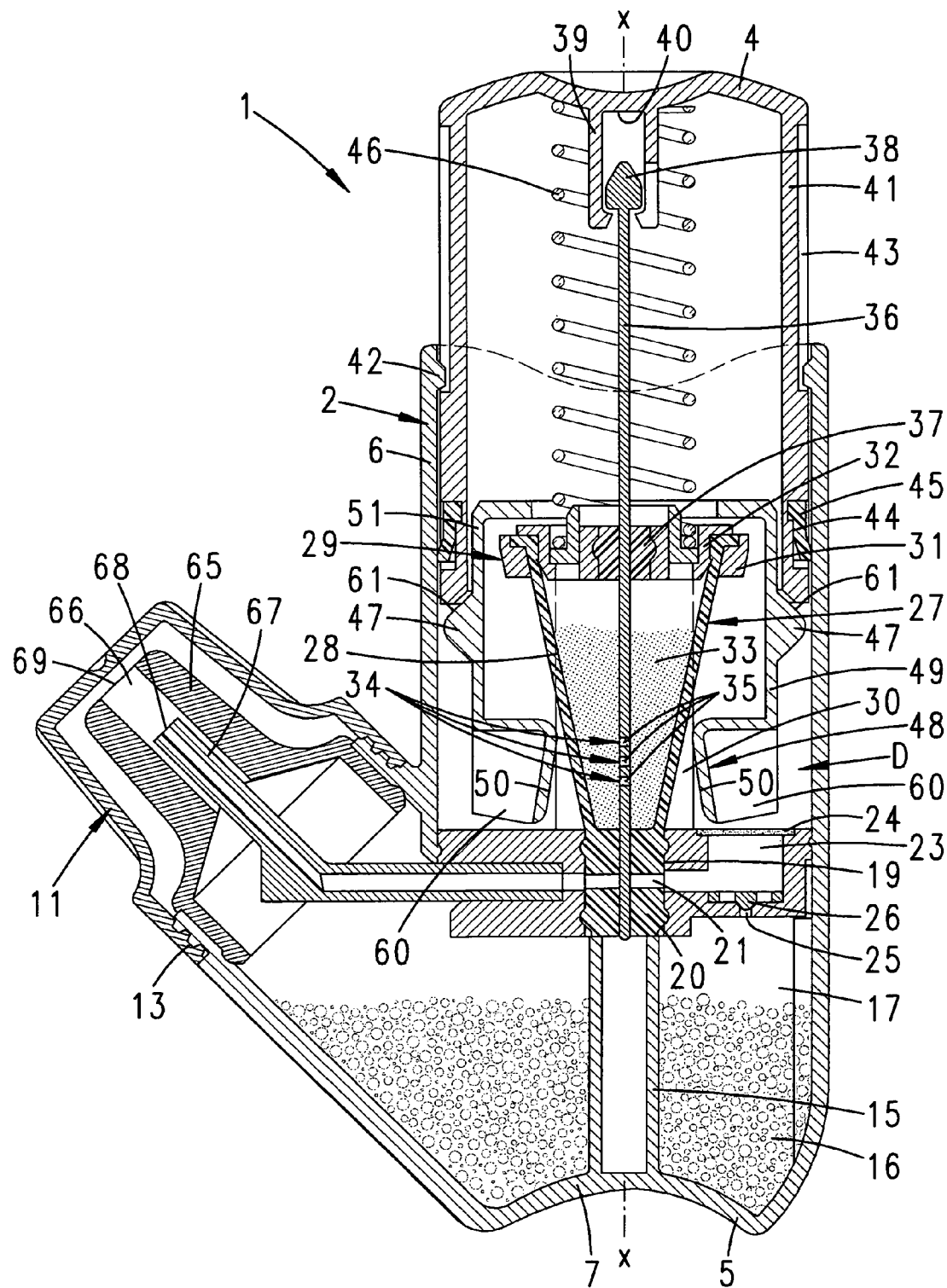
FIG. 12 shows a vertical sectional representation corresponding to FIG. 1, for the inhaler in a further embodiment for nasal inhalation.

In addition, the inhaler 1, designed for oral treatment, is also conceivable in an embodiment for nasal inhalation such as that represented for example in FIG. 12.

According to the representation in FIG. 12, in an embodiment for nasal inhalation the discharge or expulsion region is directed obliquely upward with respect to the vertical axis x, therefore including an angle in relation to the longitudinal axis x of approximately 45°. For this purpose, the housing 2 is provided with a nose tube 65, which is covered over by a screw cap 11 when the inhaler 1 is not in use in a way corresponding to the embodiment previously described.

The nose tube 65 is adapted in its longitudinal extent and its outside diameter for being introduced into a nasal opening. Centrally in the longitudinal extent of the nose tube 65, the latter is passed through by a discharge channel 66. Opening out into the latter is an end channel portion 67 of the air flow channel 21, the free end 68 of which is placed in relation to the free end 69 of the nose tube 65 such that it is set back, accordingly set back axially with respect to the axis of the body of the nose tube.

In a way corresponding to the alignment of the nose tube 65 or the axis of its body, aligned at an acute angle in relation to the longitudinal axis x, the end channel portion 67 also extends such that it is directed obliquely upward from the cross-directed straight air flow channel 21, this taking place while the free cross-section is reduced by approximately one third with respect to the cross-section of the air flow channel 21, which allows a nozzle-like configuration of the end channel portion 67.

By disposing the end channel portion 67 and the nose tube 65 in an obliquely upwardly directed manner with respect to the housing axis x, handling of the inhaler 1 with an alignment of the housing 2 along the housing axis x which is as a whole approximately vertical can be achieved for nasal inhalation.

Figure 10:
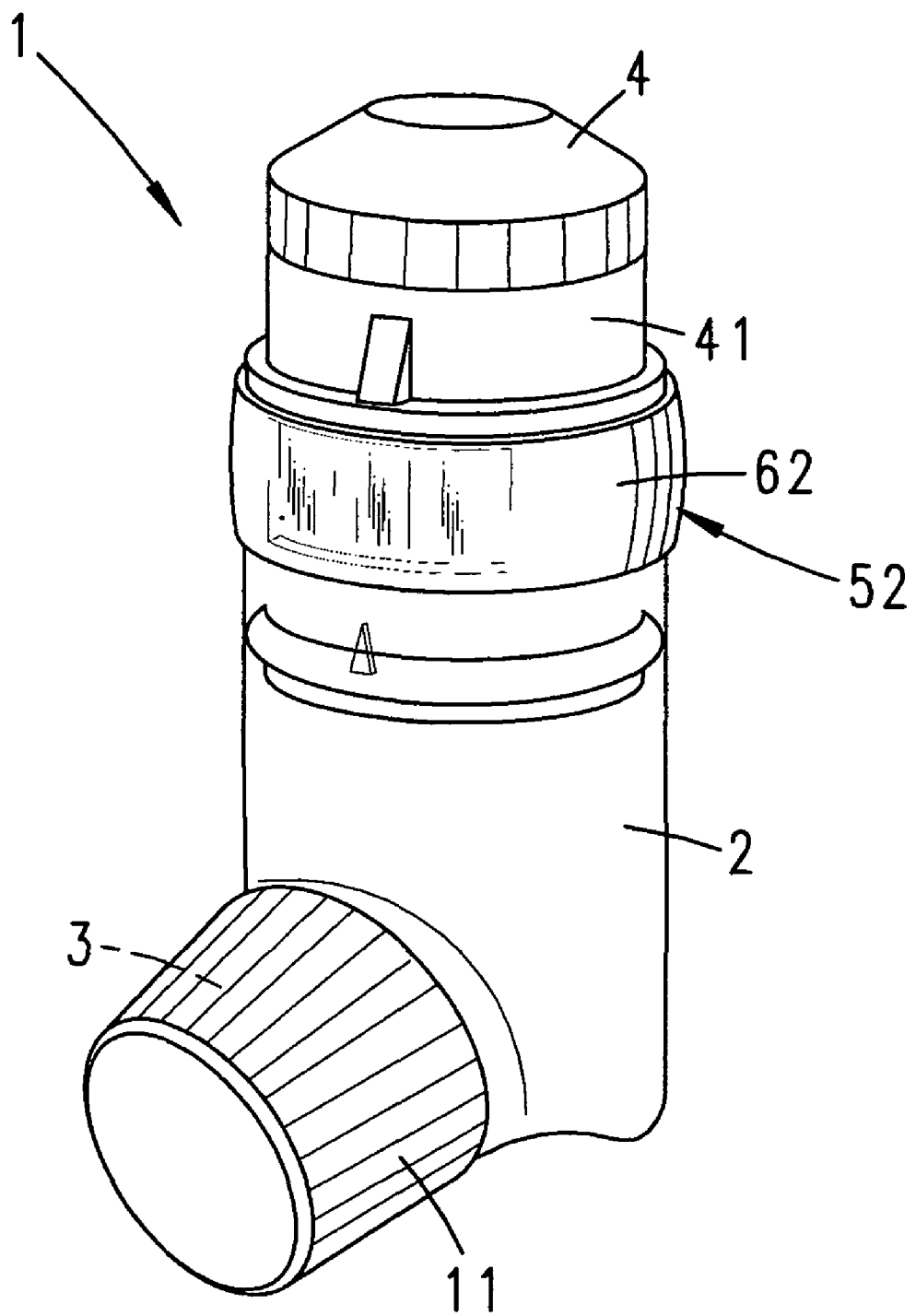
FIG. 10 shows the inhaler in a second embodiment in a perspective representation.
Figure 11:
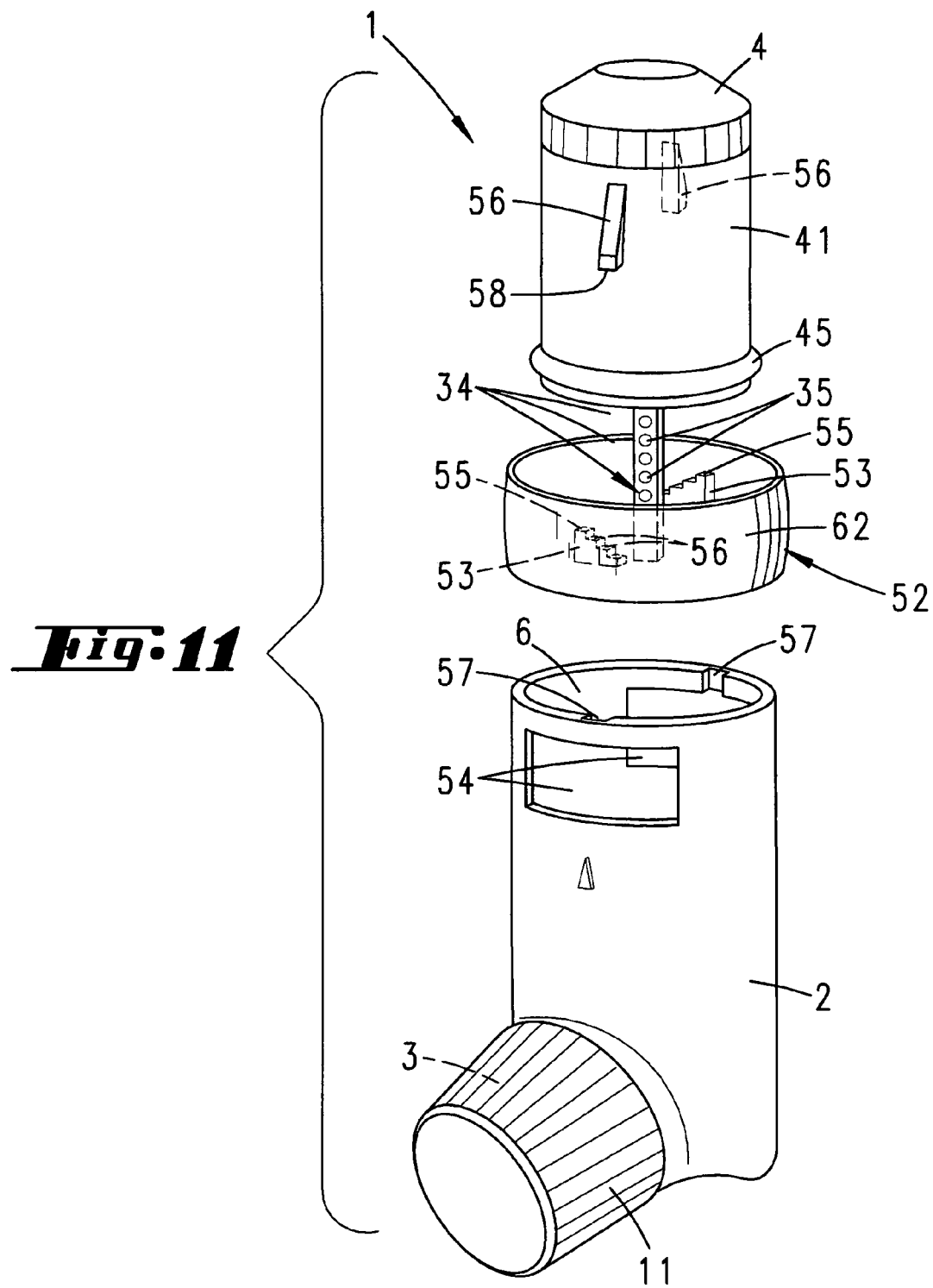
FIG. 11 shows the inhaler according to FIG. 10 in a partially exploded view.

In FIGS. 10 and 11, a second embodiment is represented, for an inhaler 1 with dosage setting.

A ring-like setting device 52 is provided, surrounding the housing 2 in the upper peripheral region that is facing the actuating button 4. The setting ring 62 of said device can be turned in stepwise manner coaxially in relation to the axis x about this axis, for example over four rotation-latching stages for setting five different dosages.

On the inner lateral surface, the annular setting device 52 is provided with stepped bodies 53, which are disposed in a diametrically opposed manner and are formed such that they pass through windows 54 of the housing 2 in a radially inwardly protruding manner.

Each stepped body 53 is provided with abutment faces 55 that are offset in relation to one another in a stepped manner. The number of step faces corresponds to the number of dosage setting possibilities. These abutment faces 55 interact with lugs 56 that are disposed in a correspondingly diametrically opposed manner on the outer lateral surface of the wall 41. These lugs are guided in correspondingly positioned grooves 57 on the inner side of the wall of the cylindrical portion 6 of the housing and are prevented from twisting with respect to the housing 2.

On actuation, a lug face 58 facing downward in the pushing-in direction of the actuating button 4 comes up against the abutment face 55 of the stepped body 53 that has been turned into the displacement path of the lug 56, whereby the displacing movement of the actuating button 4 is stopped.

This is also accompanied by the displacement of the rod 36, which in this exemplary embodiment is provided with five dosing chambers 34 disposed one after the other, being stop-limited, as a result of which the number of dosing chambers 34 that can be brought into the emptying position E can be preselected in dependence on the setting by means of the step abutments.

In a way corresponding to the preselection by means of the setting device 52, for example only two dosing chambers 34 or only the first dosing chamber 34 can be connected to the air flow channel 21 and blown out by means of applying compressed air when the inhaler 1 is actuated. In a further setting, for example all the dosing chambers 34, thus five dosing chambers 34 in the embodiment represented, can be successively brought to the air flow channel 21 and their substance portions fired out rather like a salvo.

FIGS. 13 to 19 show an inhaler 1 in a further embodiment, formed initially according to the first embodiment as an oral inhaler. An indexing mechanism 70 is provided, for registering and indicating the inhalation processes carried out. This indexing mechanism 70 is disposed in the actuating button 4 protruding above the housing 2, thus is also directly underneath the top of the actuating button 4, surrounding the drag arms 39 interacting with the driver 38 of the rod 36.

The indexing mechanism 70 substantially comprises an indexing wheel 71 and a scale ring 72, which is in positive engagement with the indexing wheel 71.

The scale ring 72 is disposed in the manner of a sleeve directly underneath the actuating top, so also concentrically in relation to the housing axis x. The peripheral wall of the scale ring is located in a radial widening of the wall 41 of the actuating button 4, and is correspondingly secured in this radial receptacle 73 of the wall 41 so as to allow turning about the housing axis x. On the outer lateral surface, the scale ring 72 is provided with a scale 74 that is not represented any more specifically, for example has such a scale printed on it. This scale 74 can be seen through a window 75 that is provided in the wall in a transitional region from the wall 41 to the top of the actuating button 4.

On the inner lateral surface of the scale ring 72, the ring is provided with radially inwardly protruding driving projections 76 centrally in terms of the vertical extent. A multiplicity of such driving projections 76, such as for example a number that corresponds to the maximum number of inhalation activations, are provided, maintaining even spacings in relation to one another when considered over the circumference. In the exemplary embodiment represented, on the other hand, a far smaller number has been chosen. Here, the way in which the scale ring 72 is driven along by means of the projections 76 takes place in a stepped-down manner.

The indexing wheel 71 interacts with these driving projections 76 in a positively engaging manner, the indexing wheel 71 being rotationally movable about an axis of rotation y aligned transversely in relation to the housing axis x, which axis y extends in the plane defined by the driving projections 76. The axis y is provided in structural terms by an axial body 77, which is held on both sides at the ends in mounting arms 78 hanging down from the top of the actuating button and protruding inward.

The indexing wheel 71 is substantially formed as a single-thread worm shaft 79, with a volute pitch, which is adapted to the spacing of two adjacent driving projections 76 in the circumferential direction. When considered in its axial direction, the worm shaft 79 is provided with such a length that, considered substantially as a whole, two to three volute portions are obtained. The respectively associated driving projection 76 enters between the flanks of the volute at the axial level of the indexing wheel 71. When the worm shaft 79 is rotationally displaced about the axis y, a displacement of the held driving projection 76 in the horizontal direction, that is to say transversely in relation to the housing axis x, correspondingly takes place.

The peripheral edge running around the end face of the volute is profiled in the manner of saw teeth, each tooth 80 having a steep flank, oriented approximately on a radius, and, to the rear thereof, a shallow flank, falling to the next-following tooth 80. In the exemplary embodiment represented, nine teeth 80 are formed over the circumference in the cross-section through the indexing wheel 71, said teeth also being dimensioned such that, when considered transversely, i.e. in the alignment of the axis y, the teeth 80 of one volute portion lie in line with the teeth 80 of the adjacent volute portion in horizontal projection. Accordingly, the respective tooth flanks of adjacent volute portions are also aligned in a common plane.

The teeth 80 interact with a counting finger 81, which has in the free end region, when considered parallel to the axis of rotation y of the indexing wheel 71, that is to say in the actuating end portion 82 interacting with the indexing wheel 71, a width which corresponds approximately to the width measured in the same direction of the indexing wheel 71.

Figure 13:
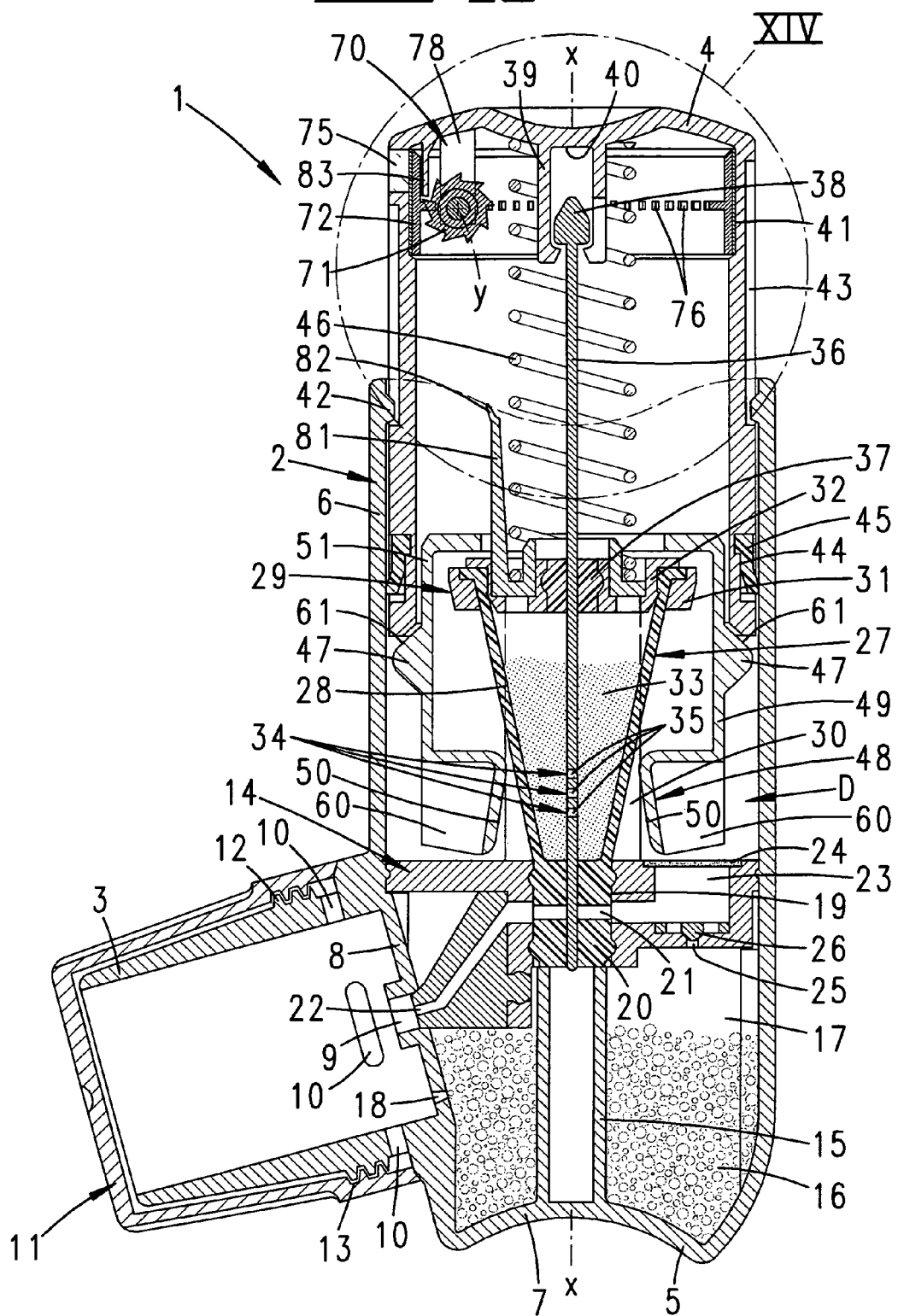
FIG. 13 shows the inhaler in a vertical sectional representation in a further embodiment with an indexing mechanism, for the initial position.
Figure 17:
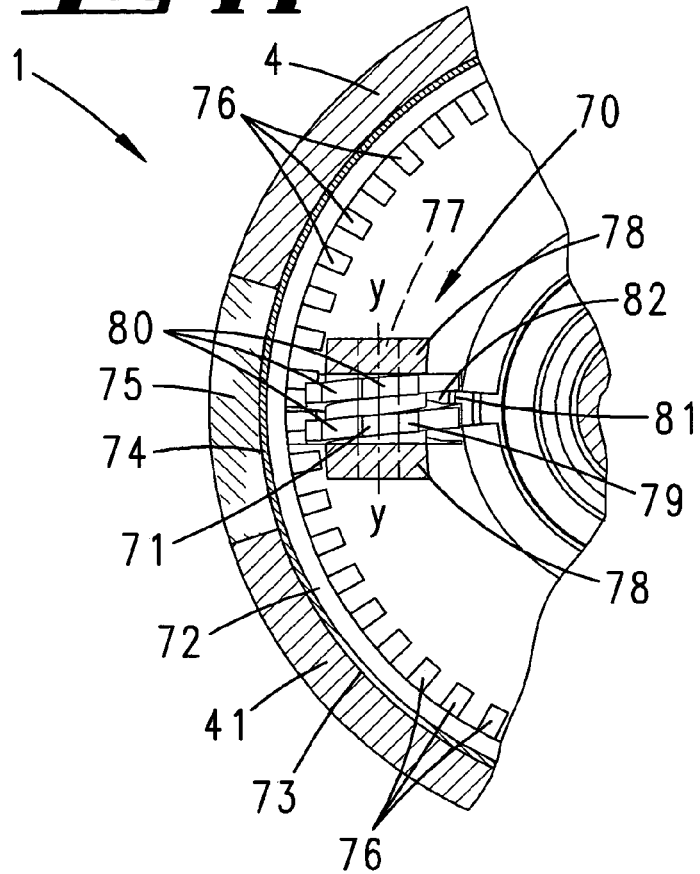
FIG. 17 shows the section along the line XVII-XVII in FIG. 15.
Figure 18:
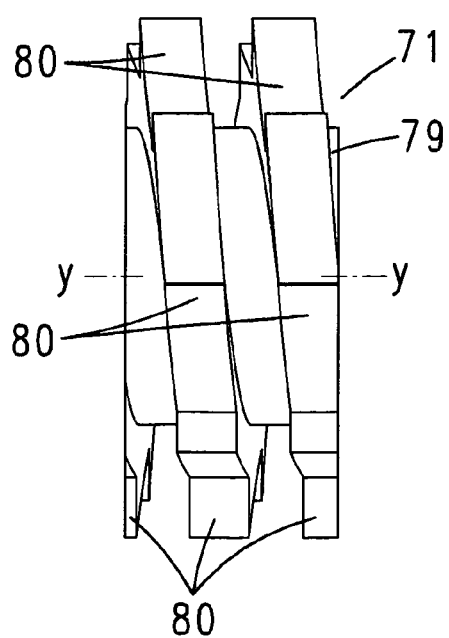
FIG. 18 shows the indexing wheel of the indexing mechanism in a representation of it on its own in side view and FIG. 19 shows the indexing wheel in a perspective representation of it on its own.
Figure 19:
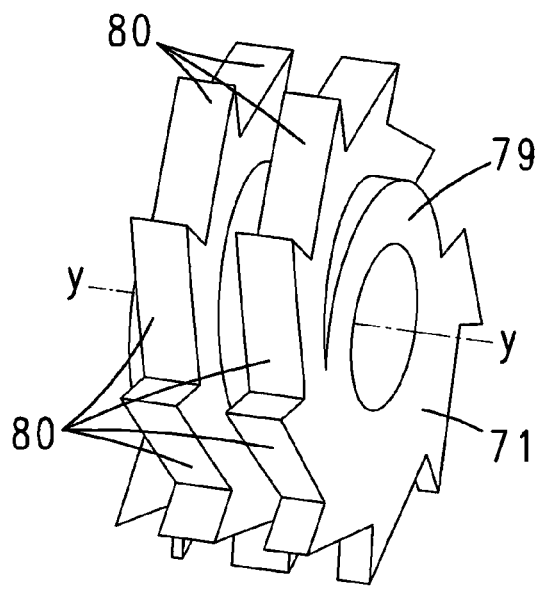

The counting finger 81 is rooted in the circular-ring-form carrier that carries the arms 49 of the thrust pieces 48, and extends upward in the manner of a rod, in parallel alignment with the housing axis x, in the direction of the indexing wheel 71, which is vertically at a distance from it in the initial position according to the representation in FIG. 13, while the previously described actuating portion 82 forming a tip is formed at the end.

Figure 5:
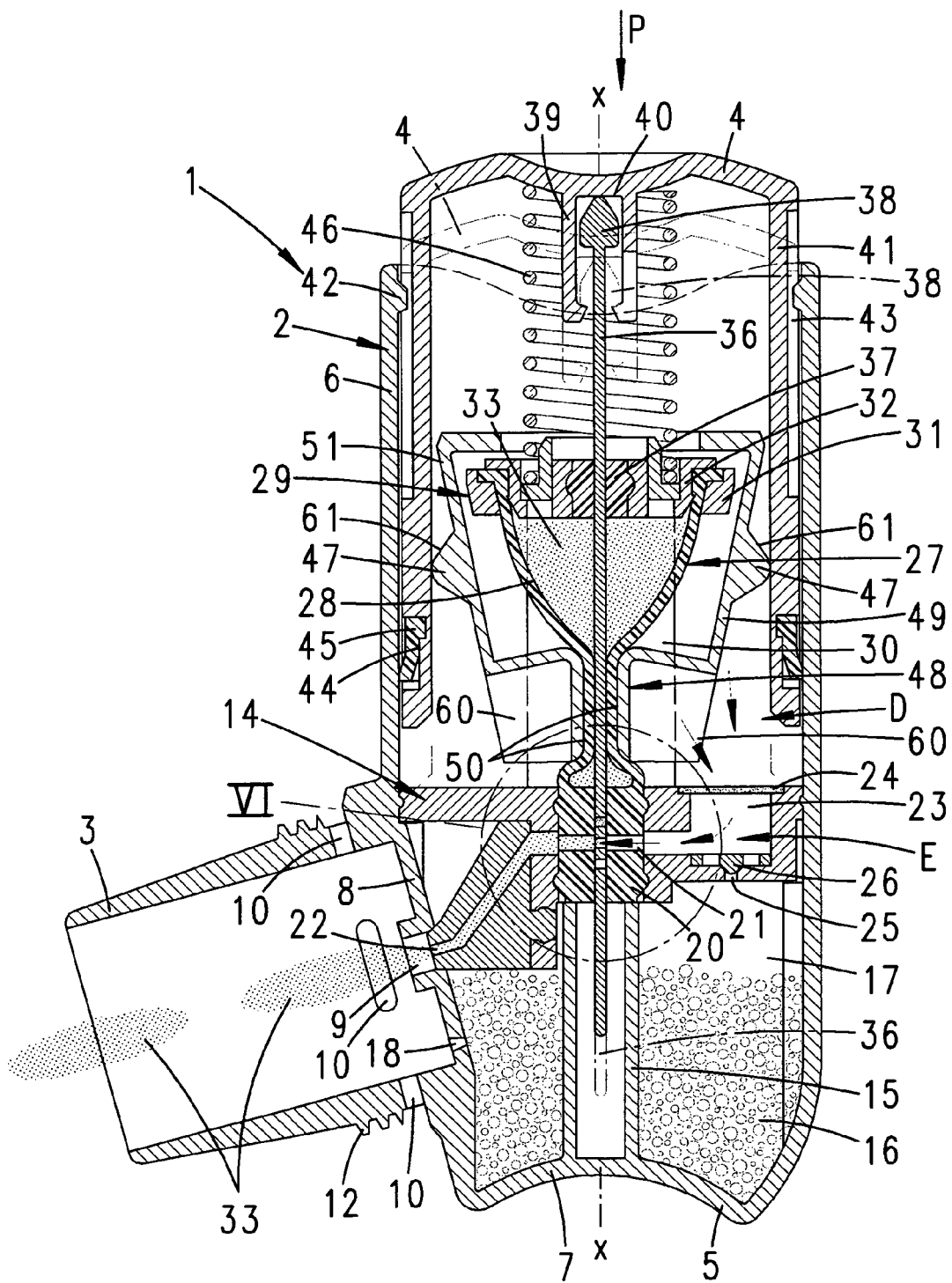
FIG. 5 shows a representation following on from FIG. 2, after further actuating displacement and dispensing of the substance.
Figure 6:
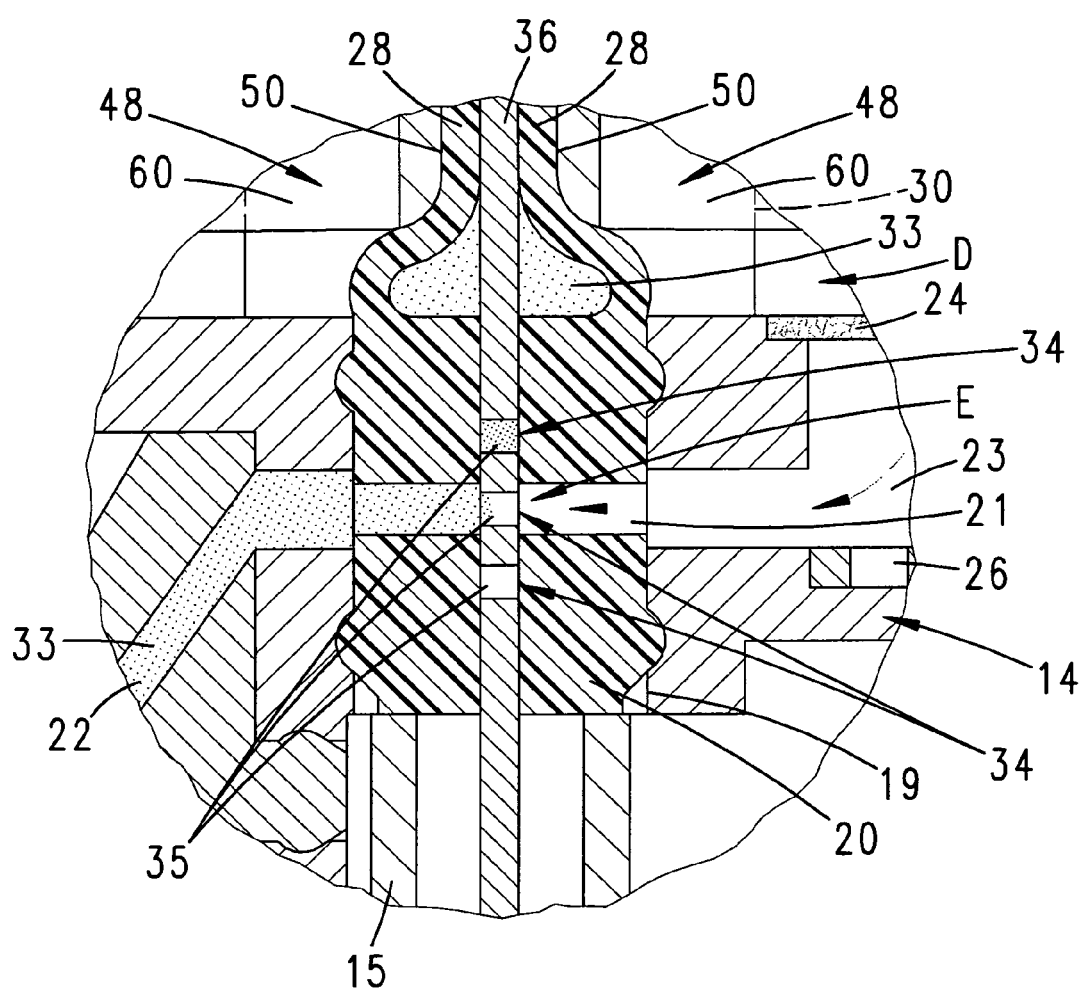
FIG. 6 shows the enlarged region VI taken from FIG. 5.
Figure 7:
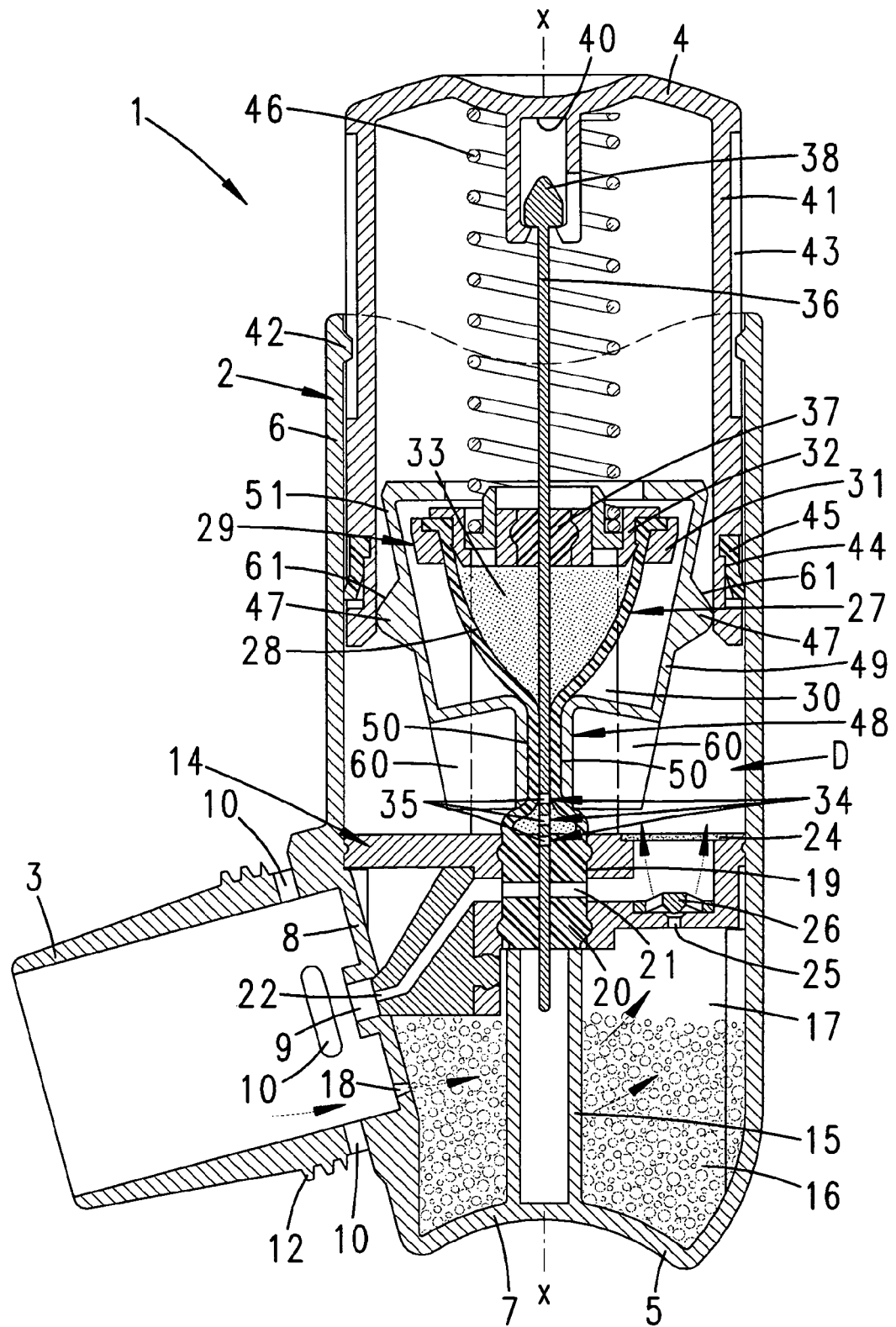
FIG. 7 shows a representation following on from FIG. 5, for an intermediate position in the course of the return displacement.
Figure 8:
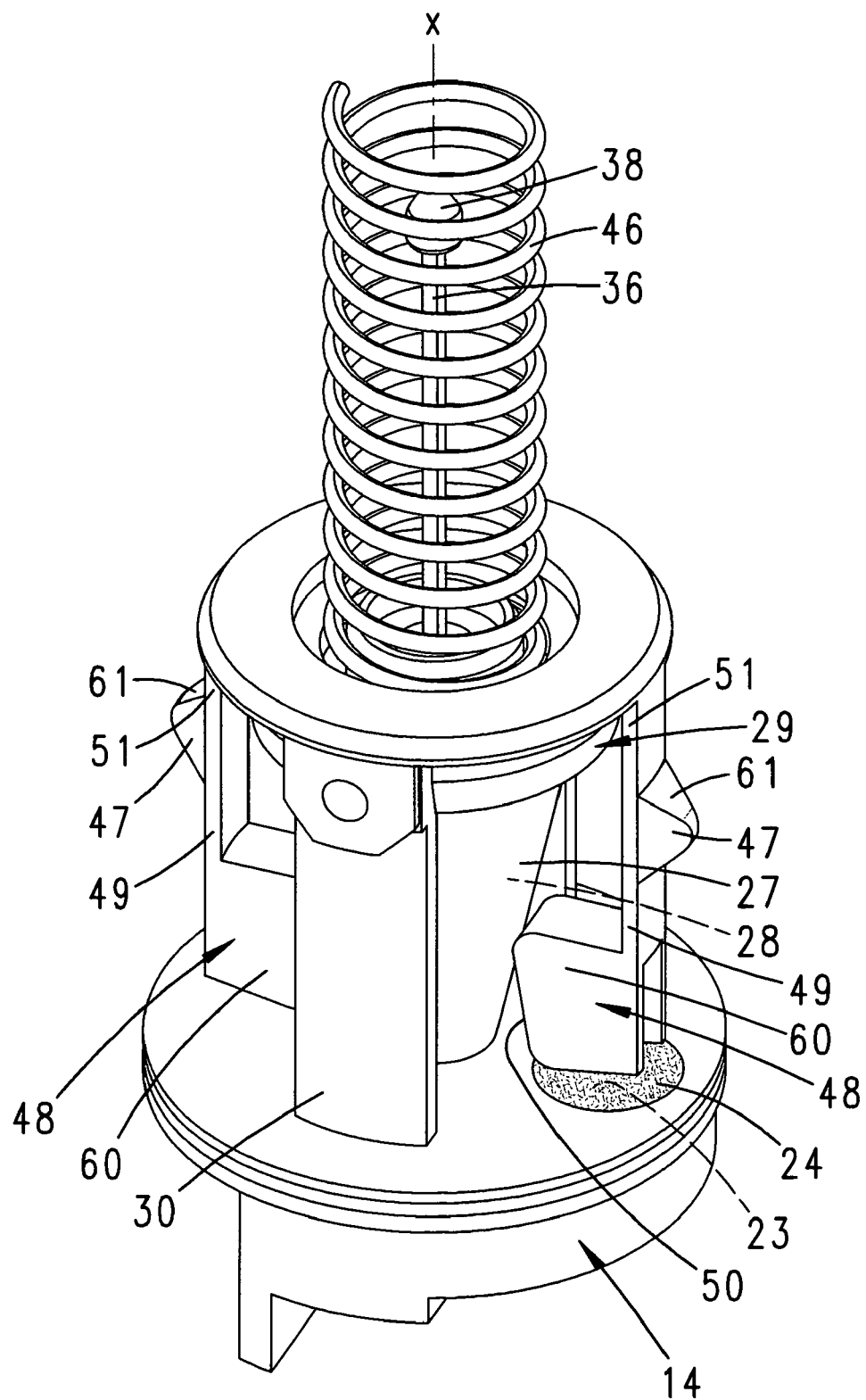
FIG. 8 shows a perspective view of a holder on its own, with a storage chamber and thrust pieces attached to it as well as a rod comprising dosing chambers and a helical return spring.
Figure 9:
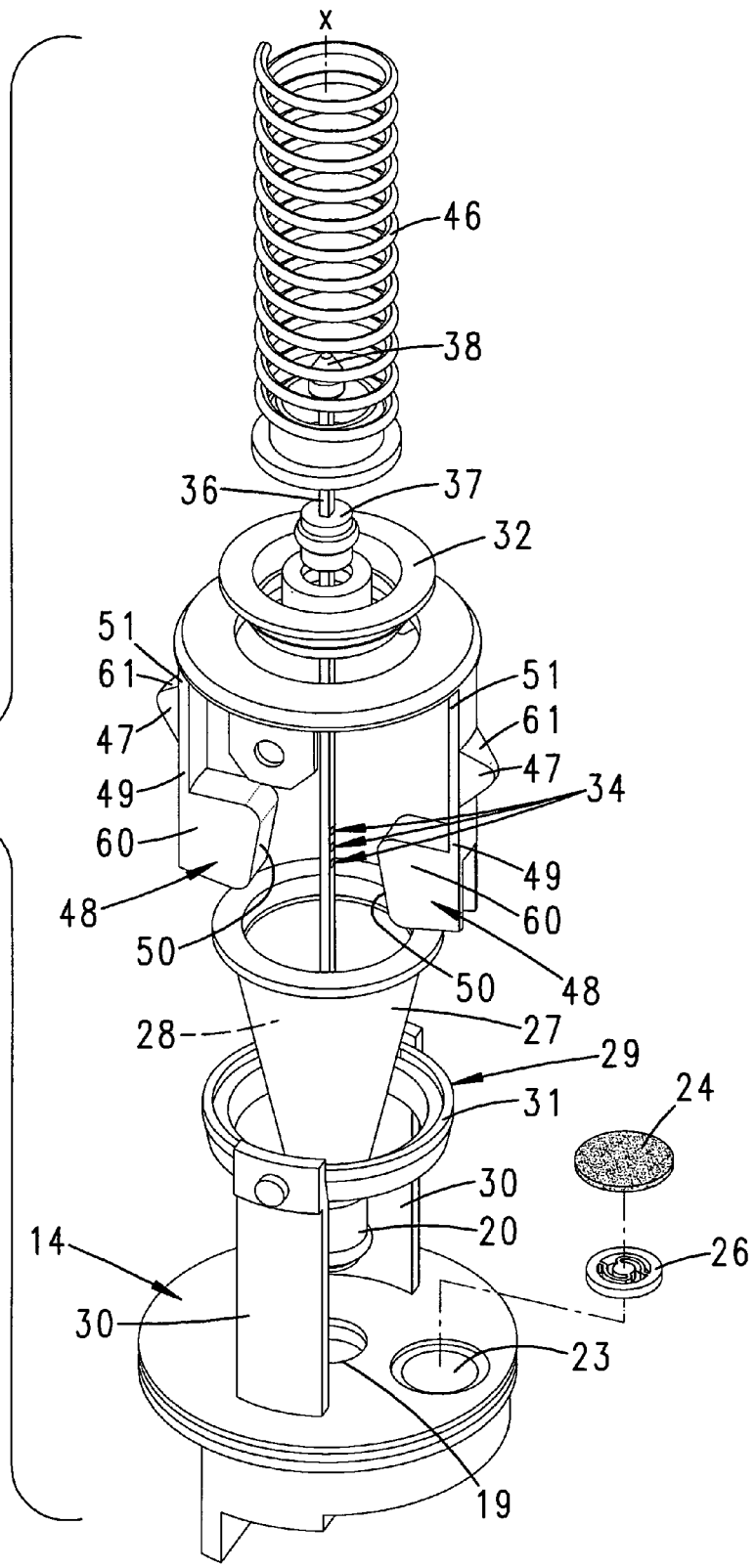
FIG. 9 shows a representation based on FIG. 8, but in an exploded view.

The vertical distance between the actuating portion 82 of the counting finger 81 and the steep flank to be actuated of a radially inwardly facing tooth 80 of the indexing wheel 71 is chosen to correspond to the displacement of the actuating button 4 from the initial position in FIG. 13 to the transfer position of the medicament from the filled dosing chamber 34 into the air flow channel 21 according to the representation in FIG. 5 or FIG. 6. Accordingly, the indexing mechanism 70 is only actuated, that is to say advanced by one position, when, in the course of the downward displacement of the actuating button 4, first the filling of the dosing chambers 34 is carried out by way of the thrust pieces 48 and after that, with further downward displacement of the actuating button 4, the blowing-out air pressure required for the abrupt blowing-out of the dosing chambers 34 is achieved. In the way described, further downward displacement of the actuating button 4 brings the dosing chambers 34 into the region of the air flow channel 21, through which the substance is abruptly blown out as a result of the air pressure that has built up. This further vertically downwardly directed actuating displacement of the button 4 leads to a rotational displacement of the indexing wheel 71 by one tooth segment. The shallow-rising tooth flanks provided at the rear make it possible for the actuating portion 82 to slide off when the actuating button 4 is displaced back into the initial position.

A retaining finger 83, which protrudes down from the top of the actuating button 4, lies opposite the actuating portion 82 and acts on a tooth 80, prevents the indexing wheel 71 from turning back counter to the predetermined direction of counting displacement.

The inhaler may contain various medicaments and/or bioactive substances for inhalation.

Any desired active therapeutic or diagnostic substance may be chosen as the bioactive substance, for example from the group comprising antiallergics, bronchodilatators, bronchoconstrictors, pulmonary surfactants, analgetics, antibiotics, leukotriene inhibitors or antagonists, anticholinergics, mast cell inhibitors, antihistamines, antiphlogistics, antineoplastics, anasthetics, antituberculotics, contrast agents, active cardiovascular substances, enzymes, steroids, genetic material, viral vectors, antisense strand reagents, proteins and peptides and combinations of these substances.

Examples of specific medicaments with which the inhaler according to the description of the patent can be filled are, inter alia, mometasone, ipratropium bromide, tiotropium and salts thereof, salmeterol, fluticasone propionate, beclomethasone dipropionate, reproterol, clenbuterol, rofleponide and salts thereof, nedocromil, sodium cromoglycate, flunisolide, budesonide, formoterol fumarate dihydrate, Symbicort®

(budesonide and formoterol), terbutaline, terbutaline sulfate, salbutamol base and sulfate, fenoterol, 3-[2-(4-hydroxy-2-oxo-3H-1,3-benzothiazol-7-yl)ethylamino]-N-[2-[2-(4-methylphenyl)ethoxy)ethyl)propane sulfonamide and hydrochloride. All the aforementioned compounds may be in a free basic form or in the form of pharmaceutical salts according to pharmaceutical practice.

Combinations of medicaments may also be used, such as for example formoterol/budesonide; formoterol/fluticasone; formoterol/mometasone; salmeterol/fluticasone; formoterol/tiotropium salts; zafirlucast/formoterol, zafirlucast/budesonide; montelucast/formoterol; montelucast/budesonide; loratadine/montelucast and loratadine/zafirlucast.

Further possible combinations are, inter alia, tiotropium and fluticasone, tiotropium and budesonide, tiotropium and mometasone, mometasone and salmeterol, formoterol and rofleponide, salmeterol and budesonide, salmeterol and rofleponide as well as tiotropium and rofleponide.

All features disclosed are (in themselves) pertinent to the invention. The disclosure content of the associated/accompanying priority documents (copy of the prior patent application) is also hereby incorporated in full in the disclosure of the application, including for the purpose of incorporating features of these documents in claims of the present application.

The invention claimed is:

1. An inhaler for a powdery medical substance, the inhaler having:
   a substance storage chamber,
   an air flow channel, and
   a rod having a plurality of cross-holes, the cross-holes being located one after the other on the rod, each cross-hole forming a dosing chamber,
   wherein each dosing chamber is able to receive a defined amount of the powdery medical substance,
   wherein each dosing chamber can be displaced from a filling position into an emptying position, each dosing chamber in the emptying position being located in the air flow channel,
   wherein the dosing chambers move into the emptying position one after the other during a discharge actuation, and
   wherein the dosing chambers can be blown out one by one by positive air pressure in the air flow channel.

2. The inhaler according to claim 1, wherein the rod is formed as a flat rod.

3. The inhaler according to claim 1, further comprising an actuating button and outer thrust pieces,
   wherein the substance storage chamber has a storage chamber wall, and
   wherein the inhaler has an inactive displacement between the actuating button and the rod with an effect that inward curving of the storage chamber wall via the outer thrust pieces takes place before the rod is taken along.

4. The inhaler according to claim 3, wherein the outer thrust pieces are provided with jaws having abutting faces lying parallel to a wide-side wall surface of the rod in a fully pivoted-in position of the outer thrust pieces.

5. The inhaler according to claim 1, further comprising:
   an actuating button,
   an outer housing having a head,
   a return spring,
   outer thrust pieces, and
   run-on slopes connected to the outer thrust pieces,
   wherein the actuating button protrudes at the head of the outer housing,
   wherein the actuating button can be displaced against the return spring, and
   wherein after a short inactive displacement of the actuating button, the actuating button pushes the rod before the actuating button and pivots the outer thrust pieces in a direction of the rod via the run-on slopes.

6. The inhaler according to claim 1, wherein the substance storage chamber has a storage chamber wall comprising elastic material, and
   wherein, when the inhaler is actuated, the storage chamber wall is made to curve in a direction of the rod.

7. The inhaler according to claim 6, wherein the storage chamber wall is made to curve, at least in a region of the dosing chambers, until the storage chamber wall abuts against the rod.

8. The inhaler according to claim 1, further comprising outer thrust pieces,
   wherein the substance storage chamber has a storage chamber wall, and
   wherein the outer thrust pieces are for inward curving of the storage chamber wall.

9. The inhaler according to claim 1, further comprising an actuating button and an outer housing,
   wherein with displacement of the actuating button in the outer housing, the positive air pressure is built up, the positive air pressure being able to blow out the powdery medical substance from the dosing chambers while the rod is in the air flow channel.

10. The inhaler according to claim 1, further comprising:
    an outer housing having an inner wall,
    an actuating button having a cup-shaped wall having an inward end region, and
    an elastic piston ring at the inward end region of the cup-shaped wall,
    wherein the inner wall of the outer housing forms a pressure cylinder for the elastic piston ring.

11. The inhaler according to claim 1, further comprising an air outlet,
    wherein a cross-section of the rod closes the air outlet.

12. The inhaler according to claim 1, further comprising an air-outlet closing point, a housing space accommodating the substance storage chamber, and an air inlet valve between the air-outlet closing point and the housing space.

13. The inhaler according to claim 1, further comprising a setting device for determining a number of dosing chambers of the plurality of dosing chambers able to be brought into the emptying position.

14. The inhaler according to claim 1, further comprising an actuating button and a setting ring with a number of steps for stopping displacing movement of the actuating button after a specific number of dosing chambers of the plurality of dosing chambers have passed through the emptying position.

15. The inhaler according to claim 1, further comprising an actuating button and a stop lug on the actuating button.

16. The inhaler according to claim 1, further comprising an outer housing having a nose tube having a free end,
    wherein the air flow channel has an end channel portion, the end channel portion being obliquely upwardly directed and having an end channel cross section smaller than a remainder cross section of a remainder of the end channel,
    wherein the air flow channel is directed straight across and continues into the end channel portion, and
    wherein the end channel portion ends within the nose tube such that the end channel portion is set back from the free end of the nose tube.

17. The inhaler according to claim 1, further comprising an indexing mechanism actuated when a blowing-out air pressure is reached.

18. The inhaler according to claim 17, further comprising a counting finger having a tip,
   wherein the indexing mechanism comprises an indexing wheel, and
   wherein the counting finger acts on the indexing mechanism in that the tip reaches the indexing wheel approximately at a beginning of a displacement of the rod into the emptying position.

19. The inhaler according to claim 18, wherein the indexing mechanism further comprises a scale ring, and
   wherein the indexing wheel turns the scale ring in the manner of a worm wheel.

* * * * *